US008709029B2

(12) United States Patent
Griffis, III et al.

(10) Patent No.: US 8,709,029 B2
(45) Date of Patent: Apr. 29, 2014

(54) APPARATUS AND METHOD FOR SECURING OCULAR TISSUE

(75) Inventors: Jack C. Griffis, III, Decatur, GA (US); Mark A. Cox, Dallas, TX (US); Douglas C. Williamson, Coppell, TX (US); Gene W. Zdenek, Northridge, CA (US); Peter J. Richardson, Buckinghamshire (GB); Michael K. Smolek, Pearl River, LA (US); Barrie D. Soloway, Long Beach, NY (US); Rex O. Bare, Lake Forest, CA (US); Andrew J. Scherer, Trabuco Canyon, CA (US); Timothy J. Payne, Santa Ana, CA (US)

(73) Assignee: Refocus Ocular, Inc., Dallas, TX (US)

( * ) Notice: Subject to any disclaimer, the term of this patent is extended or adjusted under 35 U.S.C. 154(b) by 161 days.

(21) Appl. No.: 11/827,444

(22) Filed: Jul. 11, 2007

(65) Prior Publication Data
US 2008/0091224 A1   Apr. 17, 2008

Related U.S. Application Data

(60) Provisional application No. 60/819,995, filed on Jul. 11, 2006.

(51) Int. Cl.
*A61F 9/00* (2006.01)
(52) U.S. Cl.
USPC .......................................................... 606/166
(58) Field of Classification Search
USPC ................... 606/166, 107; 351/217; 600/236; 623/5.12
See application file for complete search history.

(56) References Cited

U.S. PATENT DOCUMENTS

| 4,205,682 | A | * | 6/1980 | Crock et al. ................. 606/166 |
| 4,340,059 | A | | 7/1982 | Marinoff |
| 4,688,570 | A | | 8/1987 | Kramer et al. |
| 4,865,033 | A | * | 9/1989 | Krumeich et al. ............ 606/166 |

(Continued)

FOREIGN PATENT DOCUMENTS

| CN | 1043257 A | 6/1990 |
| EP | 0 336 065 A2 | 10/1989 |

(Continued)

OTHER PUBLICATIONS

Annex to Form PCT/ISA/206 Communication Relating to the Results of the Partial International Search dated Apr. 10, 2008 in PCT Application No. PCT/US2007/015774.

(Continued)

*Primary Examiner* — Tuan V Nguyen
*Assistant Examiner* — Sarah Simpson

(57) ABSTRACT

Various ocular fixation devices are disclosed. One ocular fixation device includes first and second rings, where at least one of the rings includes means for fixating ocular tissue of an eye. The means for fixating are arranged to grasp the ocular tissue of the eye and to release the ocular tissue of the eye based on rotation of at least one of the first and second rings. The ocular fixation device may also include one or more structures on which a surgical tool can be mounted on the ocular fixation device at one or more locations. For instance, a dome of the ocular fixation device could include one or more holes that are configured to receive one or more projections from the surgical tool. As another example, a base of the ocular fixation device could include one or more notches configured to receive a projection from the surgical tool.

26 Claims, 17 Drawing Sheets

(56) References Cited

U.S. PATENT DOCUMENTS

| | | | |
|---|---|---|---|
| 5,009,660 A | 4/1991 | Clapham | |
| 5,092,863 A | 3/1992 | Schanzlin | |
| 5,098,443 A | 3/1992 | Parel et al. | |
| 5,437,658 A * | 8/1995 | Muller et al. | 606/5 |
| 5,489,299 A | 2/1996 | Schachar | |
| 6,342,053 B1 | 1/2002 | Berry | |
| 6,527,780 B1 | 3/2003 | Wallace et al. | |
| 6,623,476 B2 | 9/2003 | Juhasz et al. | |
| 6,863,667 B2 * | 3/2005 | Webb et al. | 606/4 |
| 7,087,050 B2 | 8/2006 | LaHaye | |
| 7,189,225 B2 | 3/2007 | Rosen | |
| 7,189,248 B2 | 3/2007 | Schachar et al. | |
| 2002/0103481 A1 | 8/2002 | Webb et al. | |
| 2002/0120285 A1 | 8/2002 | Schachar et al. | |
| 2004/0054374 A1 | 3/2004 | Weber et al. | |
| 2004/0073245 A1 | 4/2004 | Schachar et al. | |
| 2004/0267294 A1 * | 12/2004 | Will | 606/166 |
| 2006/0129129 A1 | 6/2006 | Smith | |
| 2006/0241750 A1 | 10/2006 | Zdenek et al. | |
| 2006/0271025 A1 | 11/2006 | Jones et al. | |

FOREIGN PATENT DOCUMENTS

| | | |
|---|---|---|
| EP | 1033120 A2 | 9/2000 |
| EP | 1 099 432 A2 | 5/2001 |
| GB | 1456746 | 11/1976 |
| JP | 2000175954 A | 6/2000 |
| JP | 2000279441 A | 10/2000 |
| JP | 2001187081 A | 7/2001 |
| JP | 2002143209 A | 5/2002 |
| JP | 2003339756 A | 12/2003 |
| JP | 2004531344 A | 10/2004 |
| JP | 2006006605 A | 1/2006 |
| WO | WO 91/14406 A1 | 10/1991 |
| WO | WO 94/07424 A1 | 4/1994 |
| WO | WO 95/15120 A1 | 6/1995 |
| WO | WO 95/28984 A1 | 11/1995 |
| WO | WO 00/21466 A1 | 4/2000 |
| WO | WO 00/74600 A1 | 12/2000 |
| WO | WO 2006/014484 A2 | 2/2006 |

OTHER PUBLICATIONS

Notification of Transmittal of the International Search Report and the Written Opinion of the International Searching Authority, or the Declaration dated Mar. 18, 2009 in connection with PCT Application No. PCT/US2007/015816.

Communication pursuant to Article 94(3) EPC dated Aug. 2, 2011 in connection with European Patent Application No. EP 07 836 052.6.

Japanese Office Action in connection with Japanese Patent Application No. 2009-519513, May 15, 2012, 10 pages.

Notification of Transmittal of the International Search Report and the Written Opinion of the International Searching Authority, or the Declaration dated Nov. 7, 2008 in PCT Application No. PCT/US2007/015774.

"Instruments to help with those frustration situations", Surgical Solutions from Katena, 4 pages, Mar. 4, 2004.

Extended European Search Report in connection with European Patent Application No. 12172628.5, Oct. 19, 2012, 8 pages.

Office Action dated Jul. 12, 2013 in connection with U.S. Appl. No. 13/413,218.

* cited by examiner

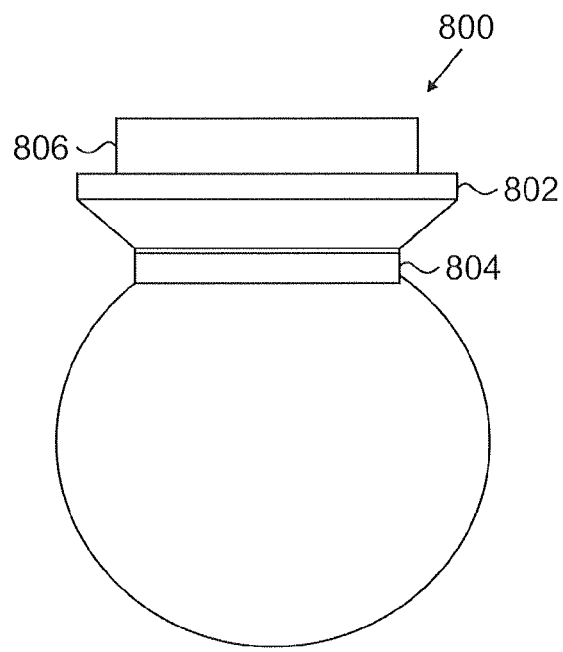
FIG. 8
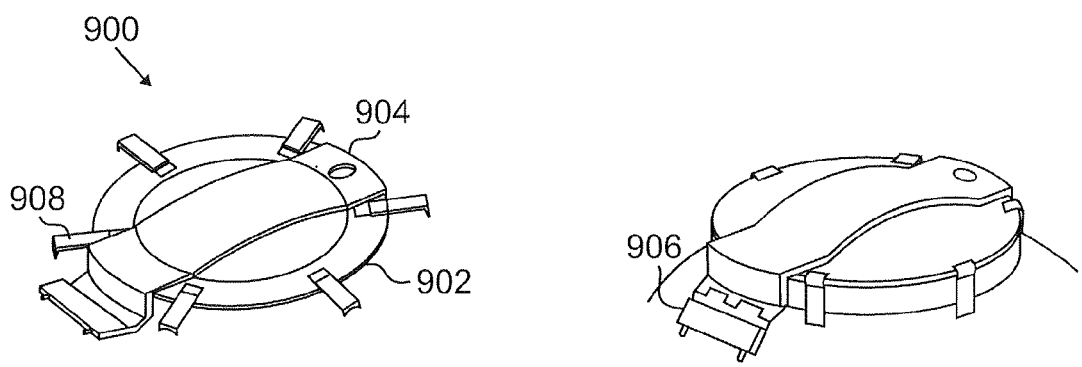
FIG. 9A
FIG. 9B
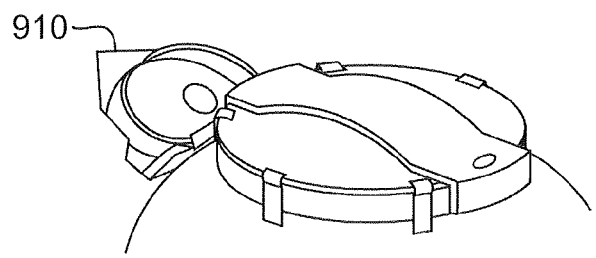
FIG. 9C

APPARATUS AND METHOD FOR SECURING OCULAR TISSUE

CROSS-REFERENCE TO RELATED PATENT DOCUMENTS

This application claims priority under 35 U.S.C. §119(e) to U.S. Provisional Patent Application No. 60/819,995 filed on Jul. 11, 2006, which is hereby incorporated by reference.

This application is related to the following U.S. patent applications and issued patents:

(1) U.S. Pat. No. 6,007,578 entitled "Scleral Prosthesis for Treatment of Presbyopia and Other Eye Disorders" issued on Dec. 28, 1999;
(2) U.S. Pat. No. 6,280,468 entitled "Scleral Prosthesis for Treatment of Presbyopia and Other Eye Disorders" issued on Aug. 28, 2001;
(3) U.S. Pat. No. 6,299,640 entitled "Scleral Prosthesis for Treatment of Presbyopia and Other Eye Disorders" issued on Oct. 9, 2001;
(4) U.S. Pat. No. 5,354,331 entitled "Treatment of Presbyopia and Other Eye Disorders" issued on Oct. 11, 1994;
(5) U.S. Pat. No. 5,465,737 entitled "Treatment of Presbyopia and Other Eye Disorders" issued on Nov. 14, 1995;
(6) U.S. Pat. No. 5,489,299 entitled "Treatment of Presbyopia and Other Eye Disorders" issued on Feb. 6, 1996;
(7) U.S. Pat. No. 5,503,165 entitled "Treatment of Presbyopia and Other Eye Disorders" issued on Apr. 2, 1996;
(8) U.S. Pat. No. 5,529,076 entitled "Treatment of Presbyopia and Other Eye Disorders" issued on Jun. 25, 1996;
(9) U.S. Pat. No. 5,722,952 entitled "Treatment of Presbyopia and Other Eye Disorders" issued on Mar. 3, 1998;
(10) U.S. Pat. No. 6,197,056 entitled "Segmented Scleral Band for Treatment of Presbyopia and Other Eye Disorders" issued on Mar. 6, 2001;
(11) U.S. Pat. No. 6,579,316 entitled "Segmented Scleral Band for Treatment of Presbyopia and Other Eye Disorders" issued on Jun. 17, 2003;
(12) U.S. Pat. No. 6,926,727 entitled "Surgical Blade for Use with a Surgical Tool for Making Incisions for Scleral Eye Implants" issued on Aug. 9, 2005;
(13) U.S. Pat. No. 6,991,650 entitled "Scleral Expansion Device Having Duck Bill" issued on Jan. 31, 2006;
(14) U.S. patent application Ser. No. 10/080,877 entitled "System and Method for Making Incisions for Scleral Eye Implants" filed on Feb. 22, 2002;
(15) U.S. patent application Ser. No. 10/443,122 entitled "System and Method for Determining a Position for a Scleral Pocket for a Scleral Prosthesis" filed on May 20, 2003;
(16) U.S. patent application Ser. No. 11/137,085 entitled "Scleral Prosthesis for Treatment of Presbyopia and Other Eye Disorders" filed on May 24, 2005;
(17) U.S. patent application Ser. No. 11/199,591 entitled "Surgical Blade for Use with a Surgical Tool for Making Incisions for Scleral Eye Implants" filed on Aug. 8, 2005;
(18) U.S. patent application Ser. No. 11/252,369 entitled "Scleral Expansion Device Having Duck Bill" filed on Oct. 17, 2005;
(19) U.S. patent application Ser. No. 11/323,283 entitled "Surgical Blade for Use with a Surgical Tool for Making Incisions for Scleral Eye Implants" filed on Dec. 30, 2005;
(20) U.S. patent application Ser. No. 11/323,284 entitled "System and Method for Making Incisions for Scleral Eye Implants" filed on Dec. 30, 2005;
(21) U.S. patent application Ser. No. 11/322,728 entitled "Segmented Scleral Band for Treatment of Presbyopia and Other Eye Disorders" filed on Dec. 30, 2005; and
(22) U.S. patent application Ser. No. 11/323,752 entitled "Segmented Scleral Band for Treatment of Presbyopia and Other Eye Disorders" filed on Dec. 30, 2005.

All of these U.S. patents and patent applications are hereby incorporated by reference.

TECHNICAL FIELD

This disclosure is generally directed to surgical devices and more specifically to an apparatus and method for securing and modifying ocular tissue.

BACKGROUND

It is often desirable or necessary to secure a patient's eye in place during ocular surgery. For example, it is possible to restore the accommodative power to a presbyopic eye by implanting scleral prostheses within the sclera of the patient's eye. It is also possible to treat glaucoma, ocular hypertension, elevated intraocular pressure, or other eye disorders by implanting scleral prostheses within the sclera of the patient's eye. During these types of procedures, an incision can be made in the sclera of the eye and extended under the surface of the sclera to form a scleral "tunnel." A scleral prosthesis can then be placed within the tunnel. Before performing a surgical procedure to implant scleral prostheses or other surgical eye procedure, the patient's eye often needs to be fixated so that the patient's eye does not move during the surgical procedure.

FIGS. 16A and 16B illustrate a conventional ocular fixation tool. This ocular fixation tool is placed on the surface of a patient's eye and is physically sutured to the sclera of the patient's eye. This ocular fixation tool includes various notches in which a surgical tool can be placed.

FIG. 17 illustrates a second conventional ocular fixation tool having a solid ring with spikes (not shown) that can be depressed into the tissue of a patient's eye. This ocular fixation tool also includes a handle rotatably coupled to the solid ring, where the handle can be used to move and position the tool. In addition, this ocular fixation tool includes a projection from the solid ring, where a surgical tool can be mounted on the projection.

FIGS. 18A and 18B illustrate a third conventional ocular fixation tool having a handle, a solid ring, and two rotatable arms. The solid ring is rotatably coupled to the handle. The two rotatable arms are coupled to or mounted on the solid ring at a common pivot point. As shown in FIG. 18A, the two rotatable arms are in the open position, and the solid ring may be placed in a desired location on a patient's eye. As shown in FIG. 18B, the two rotatable arms can then be closed, which drives prongs or other extensions on the arms into the tissue of the patient's eye. After that, the handle can be rotated sideways so that a surgeon or tool has clear access to the patient's eye through the rings. In other embodiments, the handle and the solid ring can be omitted, and the two rotatable arms could be used by themselves (the arms can be closed and opened to lock onto and release a patient's ocular tissue). In still other embodiments, the two rotatable arms could lack prongs or other extensions themselves, and the arms could be used to drive pins or other extensions on the solid ring into a patient's ocular tissue.

SUMMARY

This disclosure provides an apparatus and method for securing ocular tissue.

In a first embodiment, an apparatus includes a first ring and a second ring, where at least one of the rings includes means for fixating ocular tissue of an eye. The means for fixating are arranged to grasp the ocular tissue of the eye and to release the ocular tissue of the eye based on rotation of at least one of the rings.

In particular embodiments, the means for fixating are arranged to grasp the ocular tissue of the eye in an area of the eye associated with the limbus of the eye.

In other particular embodiments, the apparatus also includes a housing in which the first and second rings are housed and a retaining ring within the housing configured to retain the first and second rings in the housing. The housing could also include a dome configured to protect a central portion of the eye.

In yet other particular embodiments, the apparatus also includes a base configured to be placed on the ocular tissue of the eye and to retain the first and second rings. The apparatus could also include a dome configured to protect a central portion of the eye.

In still other particular embodiments, the first and second rings include tabs that extend outside of the dome and the base. The tabs may be configured to rotate at least one of the first and second rings.

In additional particular embodiments, the apparatus includes one or more mechanisms for aligning a surgical tool with a position on the eye. For example, the dome could include one or more holes configured to receive one or more projections from a surgical tool so as to align the surgical tool with a position on the eye. As another example, the base could include one or more notches, where each notch is configured to receive a projection from a surgical tool so as to align the surgical tool with a position on the eye. In addition, the base could include one or more portions that are configured to lie on the eye. The one or more portions could include one or more edges configured to allow a base of the surgical tool to be aligned against one of the edges when the projection from the surgical tool is inserted into one of the notches.

In a second embodiment, a system includes an ocular fixation device having a first ring and a second ring. At least one of the rings includes means for fixating ocular tissue of an eye, where the means for fixating are arranged to grasp the ocular tissue of the eye and to release the ocular tissue of the eye based on rotation of at least one of the rings. The system also includes a surgical tool mountable on the ocular fixation device.

In particular embodiments, the surgical tool includes a surgical blade configured to form a scleral tunnel in the ocular tissue of the eye.

In a third embodiment, a method includes placing an ocular fixation device on an eye of a patient. The ocular fixation device includes a first ring and a second ring, where at least one of the rings includes means for fixating ocular tissue of the patient's eye. The method also includes rotating at least one of the first and second rings so that the means for fixating grasp the ocular tissue of the patient's eye.

In particular embodiments, the method also includes rotating at least one of the first and second rings so that the means for fixating release the ocular tissue of the patient's eye.

In a fourth embodiment, an apparatus includes a first ring having a plurality of first teeth and a second ring having a plurality of second teeth. The first and second teeth are arranged to grasp ocular tissue of an eye and to release the ocular tissue of the eye based on rotation of at least one of the rings.

In a fifth embodiment, an apparatus includes one or more rings having means for fixating ocular tissue of an eye. The means for fixating are arranged to grasp the ocular tissue of the eye and to release the ocular tissue of the eye based on movement of at least one of the one or more rings.

In a sixth embodiment, an apparatus includes a ring configured to be placed on an eye, where the ring includes a plurality of portions for resting against a surface of the eye. The ring also includes a plurality of portions forming a plurality of notches configured to receive sutures for attaching the ring to the eye.

In a seventh embodiment, an apparatus includes a base configured to be depressed against ocular tissue of an eye. The apparatus also includes means for fixating coupled to the base and configured to be secured against the ocular tissue of the eye. The apparatus further includes a handle configured to move the means for fixating.

In an eighth embodiment, an apparatus includes a central portion configured to be placed over at least the cornea of an eye. The apparatus also includes means for fixating ocular tissue of the eye, where the means for fixating are located on the central portion. In addition, the apparatus includes a tool support attached to the central portion and configured to receive a surgical tool.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawing, in which:

FIG. 8 illustrates a sixth example ocular fixation device in accordance with this disclosure;

FIGS. 9A through 9C illustrate a seventh example ocular fixation device and an example use of the ocular fixation device in accordance with this disclosure;

DETAILED DESCRIPTION

FIGS. 1A through 1F illustrate a first example ocular fixation device 100 in accordance with this disclosure. The embodiment of the ocular fixation device 100 shown in FIGS. 1A through 1F is for illustration only. Other embodiments of the ocular fixation device 100 could be used without departing from the scope of this disclosure.

Figure 1A:
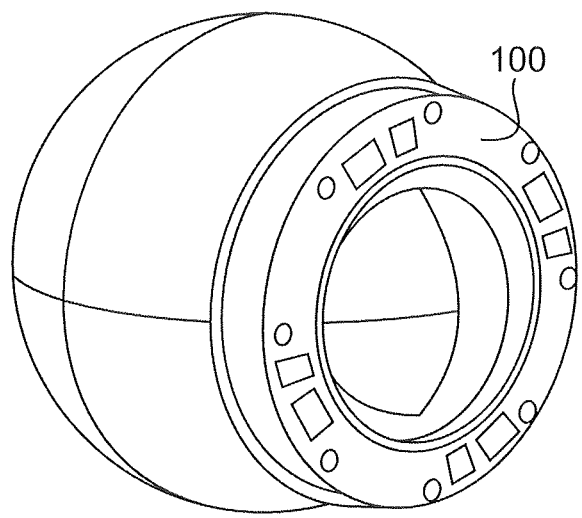
FIGS. 1A through 1F illustrate a first example ocular fixation device in accordance with this disclosure.
Figure 1B:
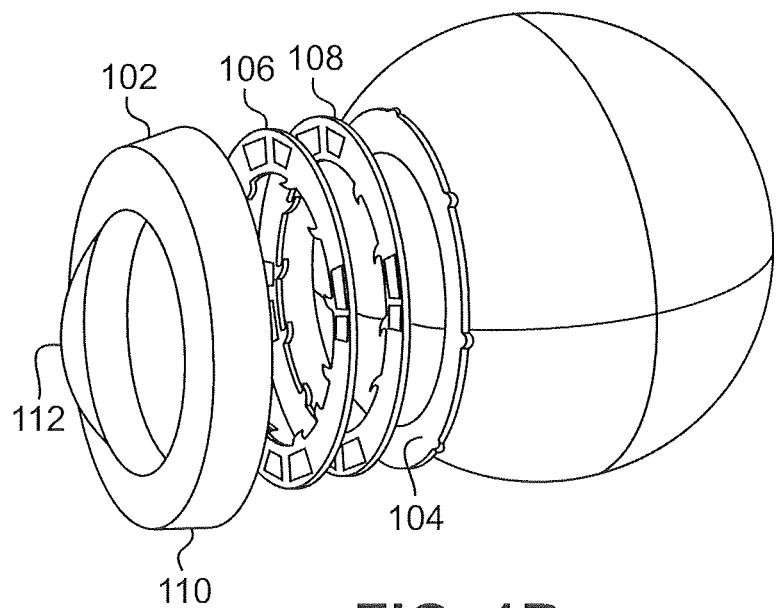

As shown in FIGS. 1A and 1B, the ocular fixation device 100 includes a body portion 102, a retention ring 104, and two locking rings 106-108. In this example, the body portion 102 includes a base 110 and a dome 112. The base 110 in this embodiment is generally circular and is used to house the retention ring 104 and the locking rings 106-108. The dome 112 represents a protective cover or shield that can be used to protect the central portion of a patient's eye. The body portion 102 could be formed from any suitable material(s), such as one or more transparent or opaque materials. The body portion 102 could also be formed using any suitable technique, such as injection molding.

The locking rings 106-108 can be inserted into the body portion 102 and the retention ring 104 can be attached to the body portion 102, which secures the locking rings 106-108 within the body portion 102. The retention ring 104 could be formed from any suitable material(s). The retention ring 104 could also be formed in any suitable manner, such as by injection molding.

Figure 1C:
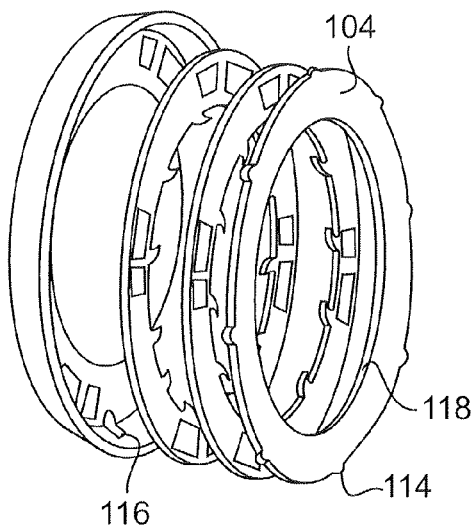

The retention ring 104 could be attached or secured to the body portion 102 in any suitable manner. For example, as shown in FIG. 1C, the retention ring 104 could include bumps 114, and the body portion 102 could include corresponding receptacles 116. In this embodiment, the retention ring 104 could be pushed into the body portion 102 until the bumps 114 engage the receptacles 116, locking the retention ring 104 in place.

As shown in FIG. 1C, the retention ring 104 could also have a slanted or tapered inner edge 118. This may help to facilitate placement of the ocular fixation tool 100 on a patient's eye. For example, the edge 118 of the retention ring 104 may be slanted so that it is substantially parallel to the portion of the patient's sclera on which the retention ring 104 rests.

Figure 1D:
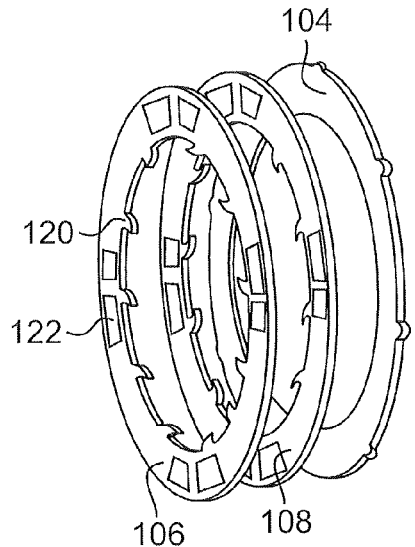
Figure 1E:
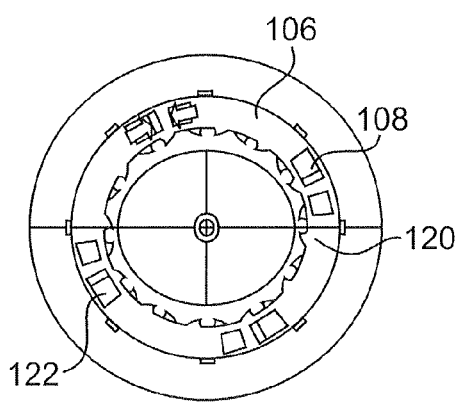

The locking rings 106-108 are used to secure the ocular fixation device 100 to a patient's eye, thereby helping to fixate and prevent movement of the patient's eye. As shown in FIGS. 1D and 1E, the locking rings 106-108 may include teeth 120. In this example, the locking rings 106-108, including the teeth 120, are substantially planar (although angled teeth could be used). Also, the teeth 120 in different locking rings 106-108 are angled towards each other. At least one of the locking rings 106-108 can rotate with respect to the other locking ring. In this way, the areas between the teeth 120 of the locking rings 106-108 can be increased and decreased. This allows the teeth 120 to grasp ocular tissue when the teeth 120 are pushed closer together. This also allows the teeth 120 to release the ocular tissue when the teeth 120 are pushed farther apart. In some embodiments, the locking rings 106-108 can be sized so that the teeth 120 attach or lock onto scleral tissue of a patient's eye (beyond the cornea and other areas in the central portion of the patient's eye). The locking rings 106-108 could be formed from any suitable material(s), such as a metal. The locking rings 106-108 could also be formed in any suitable manner, such as by photo-etching.

Figure 1F:
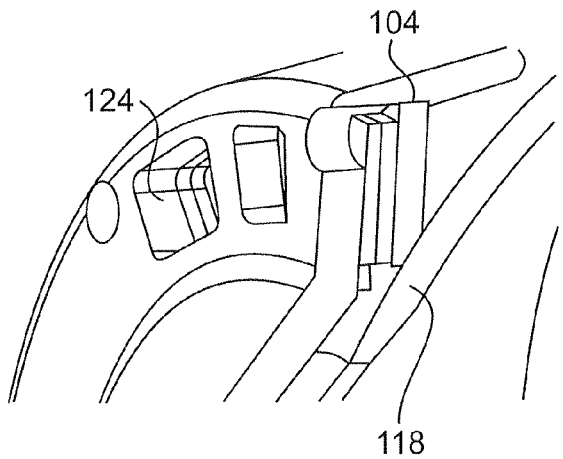

As shown in FIGS. 1D through 1F, the locking rings 106-108 include windows 122, and the body portion 102 includes corresponding windows 124. In some embodiments, a surgeon could insert a tool through one of the windows 124 and use the tool to cause one or more of the locking rings 106-108 to move. For example, the surgeon could insert a tool through one of the windows 124 and push or pull one of the locking rings 106-108, causing the openings between the teeth 120 of the locking rings 106-108 to open or close. As another example, the surgeon could insert a tool through one of the windows 124 and push both locking rings 106-108 together, causing the openings between the teeth 120 of the locking rings 106-108 to close. In other embodiments, part or all of the body portion 102 could be designed to rotate, causing the locking ring 106 to rotate with respect to the locking ring 108. This may allow, for example, the ocular fixation device 100 to be placed on a patient's eye and then rotated to lock the ocular fixation device 100 onto the patient's eye. Any other or additional technique could be used to cause the teeth 120 of the locking rings 106-108 to move with respect to each other.

Figure 2A:
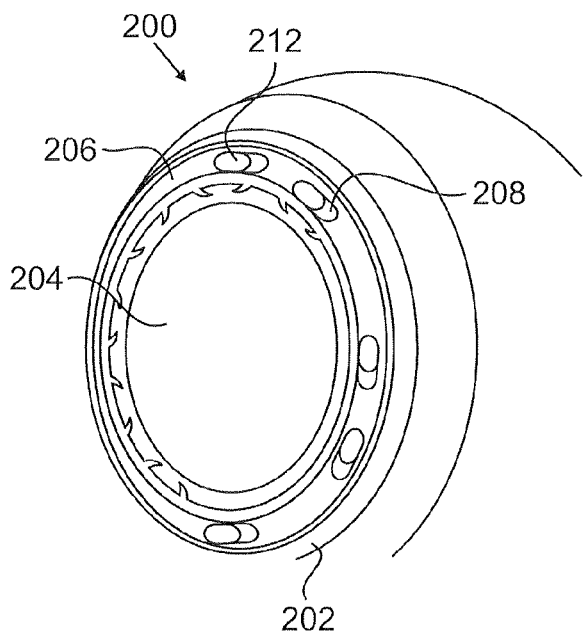
FIGS. 2A through 2C illustrate a second example ocular fixation device in accordance with this disclosure.
Figure 2B:
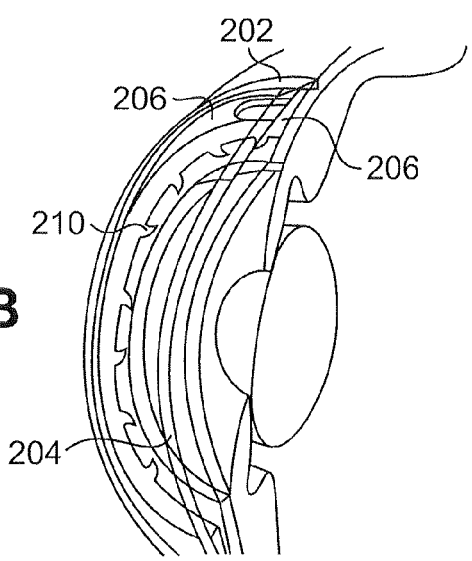
Figure 2C:
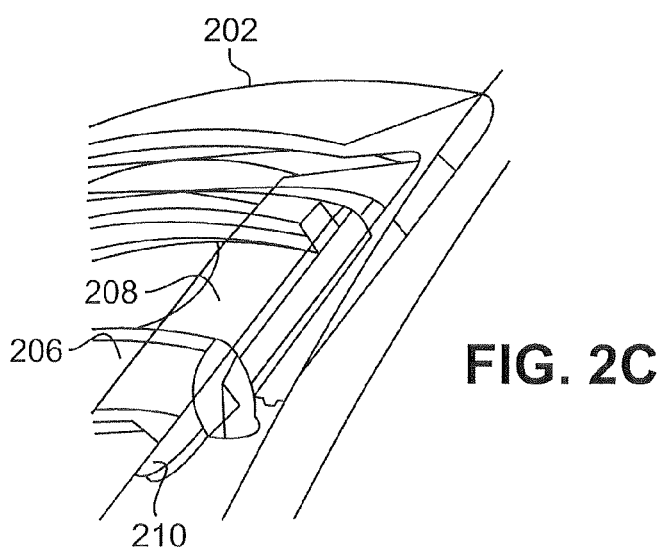

FIGS. 2A through 2C illustrate a second example ocular fixation device 200 in accordance with this disclosure. The embodiment of the ocular fixation device 200 shown in FIGS. 2A through 2C is for illustration only. Other embodiments of the ocular fixation device 200 could be used without departing from the scope of this disclosure.

The ocular fixation device 200 of FIGS. 2A through 2C operates in a similar manner as the ocular fixation device 100 of FIGS. 1A through 1F. As shown in FIG. 2A, the ocular fixation device 200 includes a base 202, a dome 204, and locking rings 206-208. Cross-sections showing additional structural details of the ocular fixation device 200 are shown in FIGS. 2B and 2C. As shown here, the base 202 is attached or secured to the dome 204 (or vice versa), helping to retain the locking rings 206-208 that are located between the base 202 and the dome 204. In this example, the cross-section of the base 202 includes a generally flat portion on which the locking rings 206-208 lie. The cross-section of the base 202 also includes a projection along its outer edge, which is attached to or helps secure the dome 204. The base 202 could further have a shape that facilitates its placement on a patient's eye, such as where the flat portion of the base 202 is slanted or sloped to approximately match a curvature of the patient's sclera. The base 202 could be formed from any suitable material(s). The base 202 could also be formed using any suitable technique, such as injection molding.

The dome 204 represents a protective cover or shield protecting the central portion of a patient's eye. The dome 204 could be formed from any suitable material(s), such as one or more transparent or opaque materials. The dome 204 could also be formed using any suitable technique, such as injection molding.

The locking rings 206-208 are located between the base 202 and the dome 204. In this example, the locking rings 206-208 include teeth 210 for attaching or locking onto ocular tissue of a patient's eye. At least one of the locking rings 206-208 can rotate with respect to the other locking ring to open and close the areas between the teeth 210 of the locking rings 206-208. This allows the teeth 210 to attach to and release ocular tissue of the patient's eye. In some embodiments, the locking rings 206-208 can be sized so that the teeth 210 attach to scleral tissue of a patient's eye. The locking rings 206-208 could be formed from any suitable material(s), such as a metal. The locking rings 206-208 could also be formed in any suitable manner, such as by photo-etching.

In this example, the locking rings 206-208 are not completely planar. Instead, each of the locking rings 206-208 includes a main section that is relatively planar and a curved section along its inner edge. The curved section of the locking ring 206 generally lies over and to the inside of the curved section of the locking ring 208. Also, the curved sections of the locking rings 206-208 include, are attached to, or carry the teeth 210 of the locking rings 206-208. In addition, the teeth 210 could be planar or angled with respect to the flat portions of the locking rings 206-208.

As shown here, each of the locking rings 206-208 includes one or more windows 212. The windows 212 can be used to identify the amount of space between the teeth 210 of the locking rings 206-208. For example, when the windows 212 of the locking rings 206-208 are aligned or nearly aligned, this may indicate that the areas between the teeth 210 of the locking rings 206-208 are substantially closed (the teeth 210 are attached or locked onto the ocular tissue of a patient's eye). Similarly, when the windows 212 of the locking rings 206-208 are not aligned very much, this may indicate that the areas between the teeth 210 of the locking rings 206-208 are substantially open (the ocular tissue of a patient's eye is not locked or has been released).

In the illustrated example, the dome 204 may cover the windows 212 of the locking rings 206-208, which could prevent the use of external tools to move the locking rings 206-208. To facilitate the attachment and release of ocular tissue by the ocular fixation device 200, one or both of the locking rings 206-208 could be rotated, such as via rotation of the dome 204 or the base 202. For example, the locking ring 206 could be fixed with respect to the dome 204, and/or the locking ring 208 could be fixed with respect to the base 202. The ocular fixation device 200 could be placed on a patient's eye, and a surgeon could rotate the dome 204 of the ocular fixation device 200. This may cause one of the locking rings 206-208 to rotate with respect to the other locking ring, thereby opening and closing the areas between the teeth 210 of the locking rings 206-208. This technique is for illustration only, and any other suitable technique could be used to attach and release ocular tissue using the ocular fixation device 200. For instance, windows could be formed in the dome 204 above the windows 212 in the locking rings 206-208, allowing the use of an external tool by the surgeon.

Figure 3A:
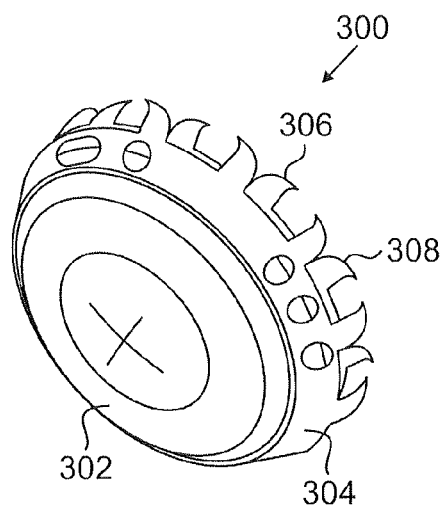
FIGS. 3A through 3C illustrate a third example ocular fixation device in accordance with this disclosure.
Figure 3B:
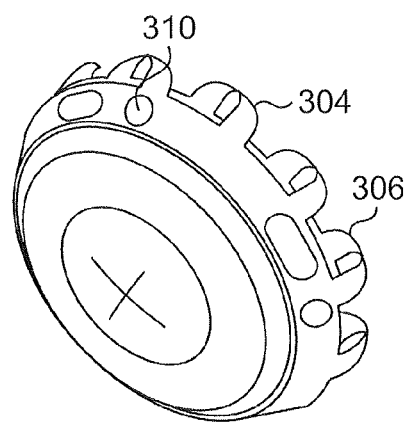
Figure 3C:
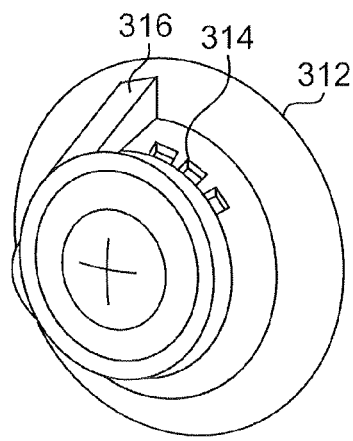

FIGS. 3A through 3C illustrate a third example ocular fixation device 300 in accordance with this disclosure. The embodiment of the ocular fixation device 300 shown in FIGS. 3A through 3C is for illustration only. Other embodiments of the ocular fixation device 300 could be used without departing from the scope of this disclosure.

As shown in FIG. 3A, the ocular fixation device 300 includes a dome 302 and locking rings 304-306. Once again, the dome 302 protects the central portion of a patient's eye and can be formed from any suitable material(s) and in any suitable manner. In this example, the dome 302 is transparent and includes a mark used to center the dome 302 on the patient's eye, although other embodiments could be used. Also, the locking rings 304-306 include teeth 308 that are shaped and positioned so that they are angled towards each other. This allows the teeth 308 of the locking rings 304-306 to attach or lock onto the ocular tissue (such as the scleral tissue) of a patient's eye. As shown in FIGS. 3A and 3B, at least one of the locking rings 304-306 is rotatable with respect to the other to open and close the areas between the teeth 308.

In this example, the locking rings 304-306 include windows 310, which can provide an indication of whether (and to what extent) the locking rings 304-306 are locked onto ocular tissue. For example, when the locking rings 304-306 are opened (not attached to ocular tissue), the windows 310 in the locking rings 304-306 may be at least partially aligned. When the locking rings 304-306 are closed (locked onto ocular tissue), the windows 310 in the locking rings 304-306 are not aligned, and the windows 310 in the locking ring 306 might be hidden.

As shown in FIG. 3C, the ocular fixation device 300 can further include a housing 312. The housing 312 holds the locking rings 304-306 and the dome 302 of the ocular fixation device 300. The housing 312 may also allow a surgeon to rotate at least one of the locking rings 304-306. In this example, the housing 312 includes windows 314 and connection points 316. The windows 314 in the housing 312 may be aligned with the windows 310 in the locking ring 304. This allows the surgeon to determine to what extent the locking rings 304-306 are opened or closed (since the housing 312 otherwise hides or covers the locking rings 304-306). The connection points 316 represent areas where a surgical tool can be attached to the housing 312 (described in more detail below), although the connection points 316 can be omitted if desired. The housing 312 can be formed from any suitable material(s) and in any suitable manner. The housing 312 can also have any suitable shape or arrangement.

In this example, the locking rings 304-306 have more of a cylindrical shape (although it need not have a true cylindrical shape and can, for example, have slanted sides). That is, the major surface of each locking ring 304-306 extends along and rotates around a central axis through the center of that locking ring 304-306.

Although FIGS. 1A through 3C illustrate three examples of ocular fixation devices, various changes may be made to FIGS. 1A through 3C. For example, the relative sizes and dimensions of the features of the ocular fixation devices are for illustration only and can be altered in any suitable manner. Also, various features shown and described with respect to one of the ocular fixation devices could be used with other ocular fixation devices. As a particular example, the locking rings 206-208 of the ocular fixation device 200 could be used with the ocular fixation device 100. As another particular example, the same or similar housing 312 used with the ocular fixation device 300 could be used with the other ocular fixation devices 100 and 200. In addition, the dome could be omitted from an ocular fixation device, such as when the ocular fixation device is used to secure a patient's eye during corneal surgery or other surgical procedure.

FIGS. 4A through 4I illustrate an example use of an ocular fixation device during creation of a scleral tunnel for receiving a scleral prosthesis in accordance with this disclosure. The example use shown in FIGS. 4A through 4I is for illustration only. An ocular fixation device could be used in any other suitable manner (including only to fixate a patient's eye) without departing from the scope of this disclosure.

As shown in FIGS. 4A through 4I, a surgical tool 450 is used, in conjunction with an ocular fixation device 400, to form incisions in a patient's eye. In this example, the ocular fixation device 400 represents the ocular fixation device 300, although any other suitable ocular fixation device could be used.

Figure 4A:
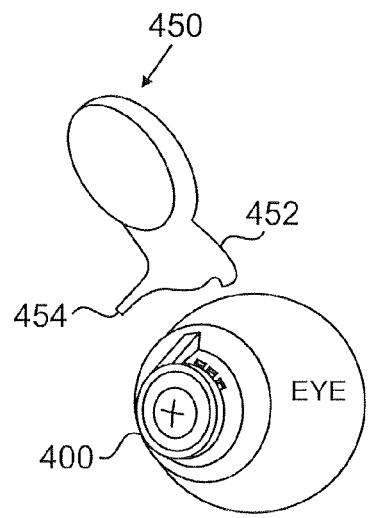
FIGS. 4A through 4I illustrate an example use of an ocular fixation device during creation of a scleral tunnel for receiving a scleral prosthesis in accordance with this disclosure.
Figure 4B:
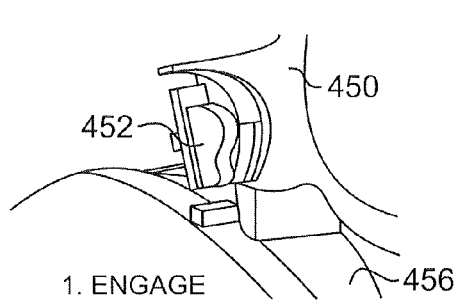
Figure 4C:
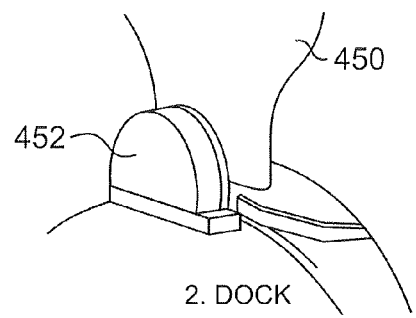
Figure 4D:
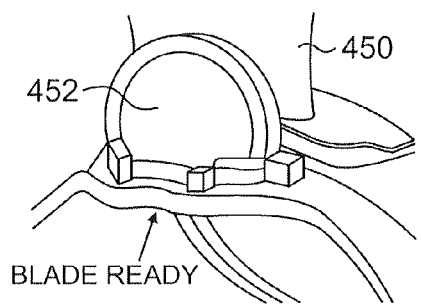
Figure 4E:
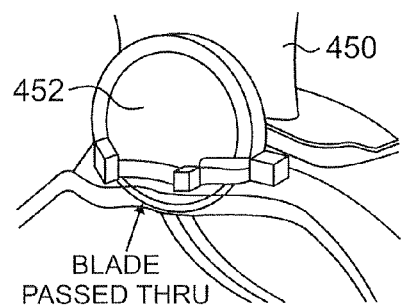

In this example, the surgical tool 450 includes a surgical blade 452 and a connecting portion 454. As shown in FIGS. 4A through 4C, the connecting portion 454 of the surgical tool 450 can engage connection points 456 of a housing associated with the ocular fixation device 400, thereby mounting the surgical tool 450 on the ocular fixation device 400. After that, as shown in FIGS. 4B through 4E, the surgical tool 450 can be rotated into position, and the surgical blade 452 can be rotated into and out of the patient's sclera to form a scleral tunnel. This process could then be repeated by mounting the surgical tool 450 at a different connection point 456. As a particular example, four scleral tunnels could be formed in a patient's eye using this technique.

In some embodiments, the surgical tool 450 is removed from the ocular fixation device 400 after one or more scleral tunnels have been formed but before one or more scleral prostheses are implanted in the tunnels. The ocular fixation device 400 could also be removed from the patient's eye before or after the scleral prostheses are implanted in the scleral tunnels.

In other embodiments, the ocular fixation device 400 and the surgical tool 450 could be used to facilitate implantation of a scleral prosthesis in a scleral tunnel. For example, as shown in FIGS. 4F through 4I, the surgical tool 450 could be configured to deposit a scleral prosthesis into a scleral tunnel during formation of the scleral tunnel. In this example, the surgical blade 452 includes a central portion 460, a curved cutting blade 462, and two hub arms 464a-464b. The central portion 460 is connected to the surgical tool 450 and can be rotated in multiple directions to move the cutting blade 462 into and out of the scleral tissue of a patient's eye. The hub arms 464a-464b couple the central portion 460 to the cutting blade 462, helping to translate rotation of the central portion 460 into movement of the cutting blade 462.

Figure 4F:
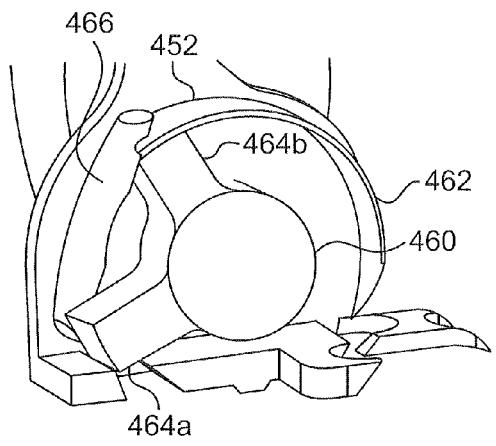
Figure 4G:
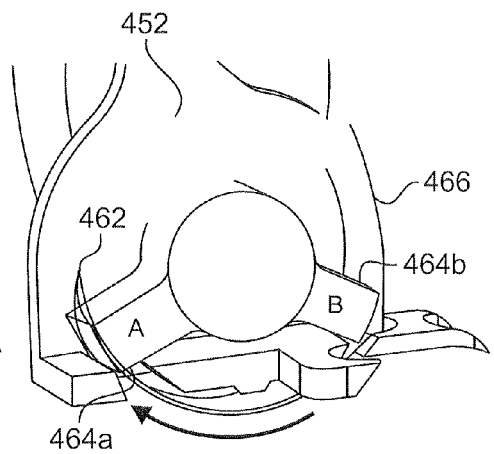
Figure 4H:
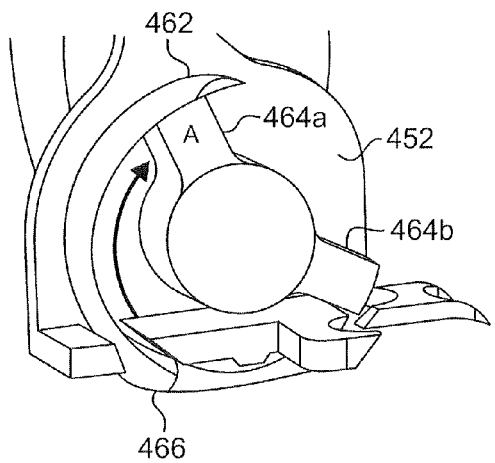
Figure 4I:
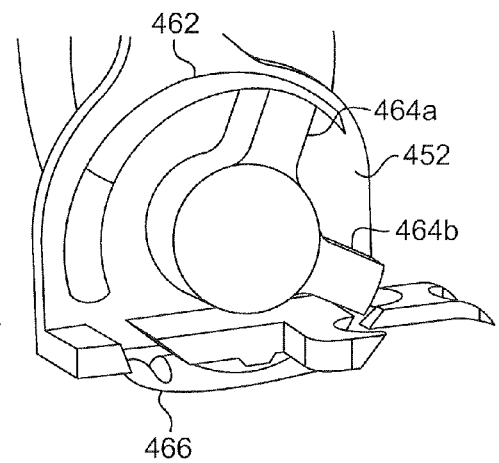

A prosthesis 466 is engaged with the tail end of the cutting blade 462. The prosthesis 466 could represent any suitable prosthesis, such as any of the prostheses disclosed in the above-incorporated patent documents. As shown in FIGS. 4F and 4G, the cutting blade 462 is initially rotated through the scleral tissue of a patient's eye using the hub arm 464b. Eventually, the hub arm 464a engages with the tip of the cutting blade 462, and the hub arm 464b disengages from the cutting blade 462. As shown in FIGS. 4H and 4I, the hub arm 464a then continues to rotate the cutting blade 462 through the scleral tissue and out of the newly formed scleral tunnel. In this example, the prosthesis 466 is pulled into the scleral tunnel upside-down by the surgical blade 452 and disengages from the cutting blade 462. The prosthesis 466 can then be rotated to properly position the prosthesis 466 in the newly-formed scleral tunnel.

The technique shown in FIGS. 4F through 4I is for illustration only. Any other suitable technique could be used to implant a scleral prosthesis into a scleral tunnel, whether or not the implantation occurs using an ocular fixation device or a surgical tool mounted on an ocular fixation device.

Although FIGS. 4A through 4I illustrate one example use of an ocular fixation device during creation of a scleral tunnel for receiving a scleral prosthesis, various changes may be made to FIGS. 4A through 4I. For example, the surgical tool 450 could be attached to or mounted on the ocular fixation device 400 in any suitable manner. Also, the same or similar techniques could be used to form incisions in other portions of a patient's eye. In addition, any other suitable surgical tool could be used in conjunction with an ocular fixation device, or no surgical tool could be used with an ocular fixation device.

Figure 5A:
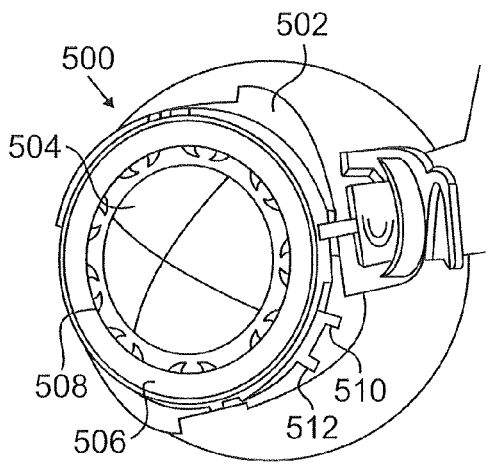
FIGS. 5A through 5C illustrate a fourth example ocular fixation device and an example use of the ocular fixation device in accordance with this disclosure.
Figure 5B:
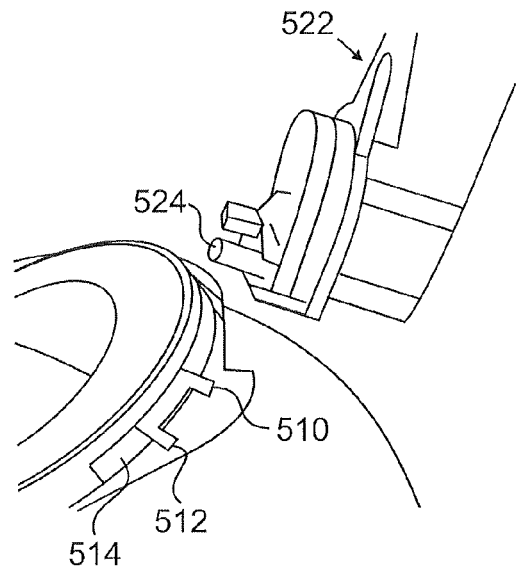
Figure 5C:
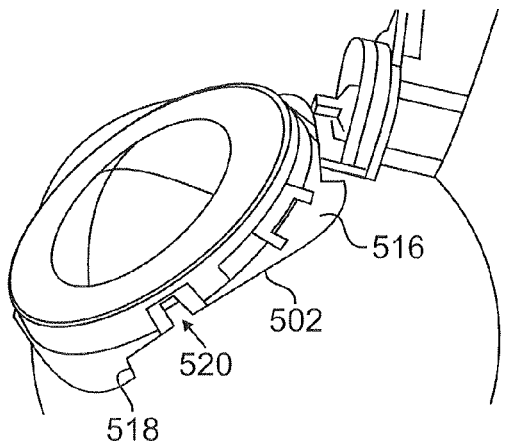

FIGS. 5A through 5C illustrate a fourth example ocular fixation device 500 and an example use of the ocular fixation device 500 in accordance with this disclosure. The embodiment of the ocular fixation device 500 and its use shown in FIGS. 5A through 5C are for illustration only. Other embodiments of the ocular fixation device 500 and uses of the ocular fixation device 500 could be used without departing from the scope of this disclosure.

As shown in FIG. 5A, the ocular fixation device 500 is similar to the ocular fixation device 200 of FIGS. 2A through 2C. The ocular fixation device 500 includes a base 502, a dome 504, and locking rings 506-508. In this example, the base 502 is attached or secured to the dome 504 (or vice versa), and the locking rings 506-508 are secured between the base 502 and the dome 504.

In this example embodiment, the locking rings 506-508 include tabs 510-512, respectively. The tabs 510-512 extend outside of the base 502 and the dome 504. For example, as shown in FIG. 5B, one or more gaps 514 could exist between the base 502 and the dome 504, and the tabs 510-512 may extend through one or more of the gaps 514. The tabs 510-512 can be used to control the opening and closing of the teeth on the locking rings 506-508. For instance, the tabs 510-512 can be pulled apart to open the teeth on the locking rings 506-508, and the tabs 510-512 can be pushed together to close the teeth on the locking rings 506-508.

As shown here, the base 502 of the ocular fixation device 500 includes portions 516 that project from the main body of the ocular fixation device 500 and that are arranged to lie generally on a patient's eye. The portions 516 include straight edges or guides 518, and the base 502 also includes notches 520. The guides 518 and the notches 520 are used to align a surgical tool 522 during a surgical procedure. For example, the surgical tool 522 could include a projection 524, which can be inserted into each of the notches 520 of the ocular fixation device 500. Also, the surgical tool 522 can be positioned so that its base is aligned with one of the straight guides 518 of the ocular fixation device 500. The surgical tool 522 can then be used to form an incision in the patient's eye, such as a scleral tunnel for receiving a scleral prosthesis. In this particular example, the ocular fixation device 500 includes guides 518 and notches 520 in four locations, although any other suitable number of locations could be supported.

In this way, the ocular fixation device 500 serves to secure the position of the patient's eye during a surgical procedure. At the same time, the ocular fixation device 500 facilitates the placement of the surgical tool 522 in the appropriate locations on the patient's eye.

Although FIGS. 5A through 5C illustrate a fourth example of an ocular fixation device 500 and an example use of the ocular fixation device 500, various changes may be made to FIGS. 5A through 5C. For example, the relative sizes and dimensions of the features of the ocular fixation device 500 are for illustration only and can be altered in any suitable manner. Also, the guide mechanisms described above (the straight guides 518 and the notches 520) could be used with any other ocular fixation device and any other surgical tool.

Figure 6A:
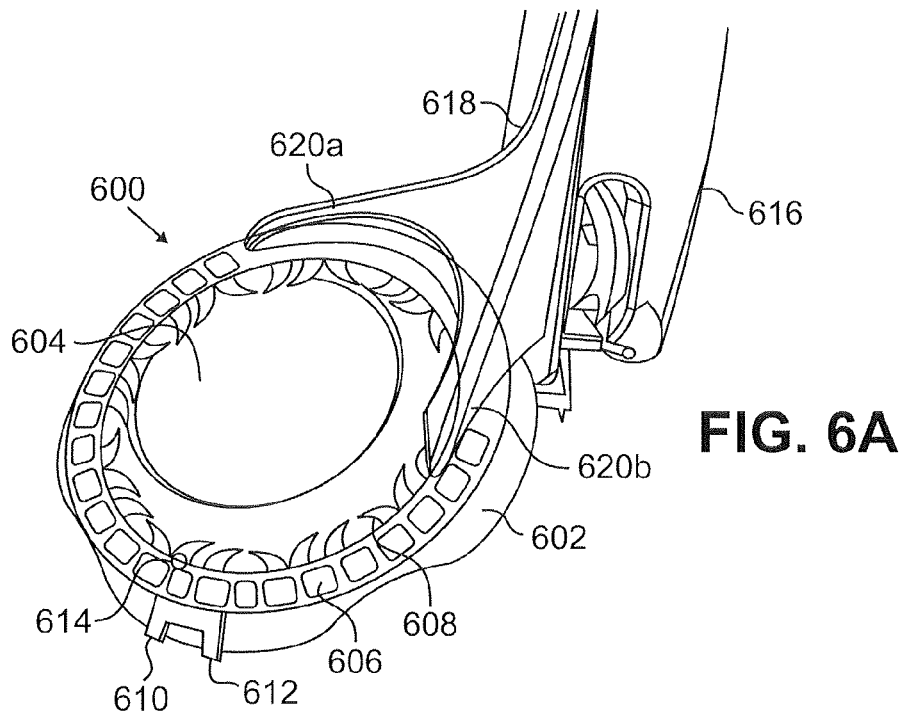
FIGS. 6A through 6C illustrate a fifth example ocular fixation device and an example use of the ocular fixation device in accordance with this disclosure.
Figure 6B:
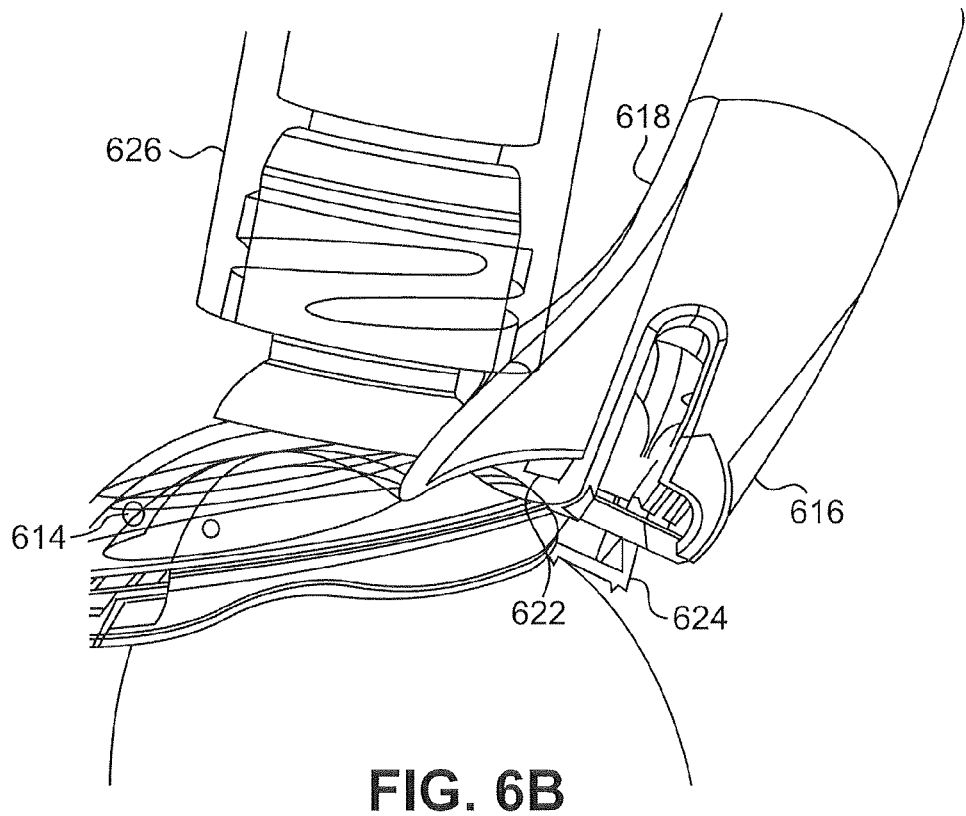
Figure 6C:
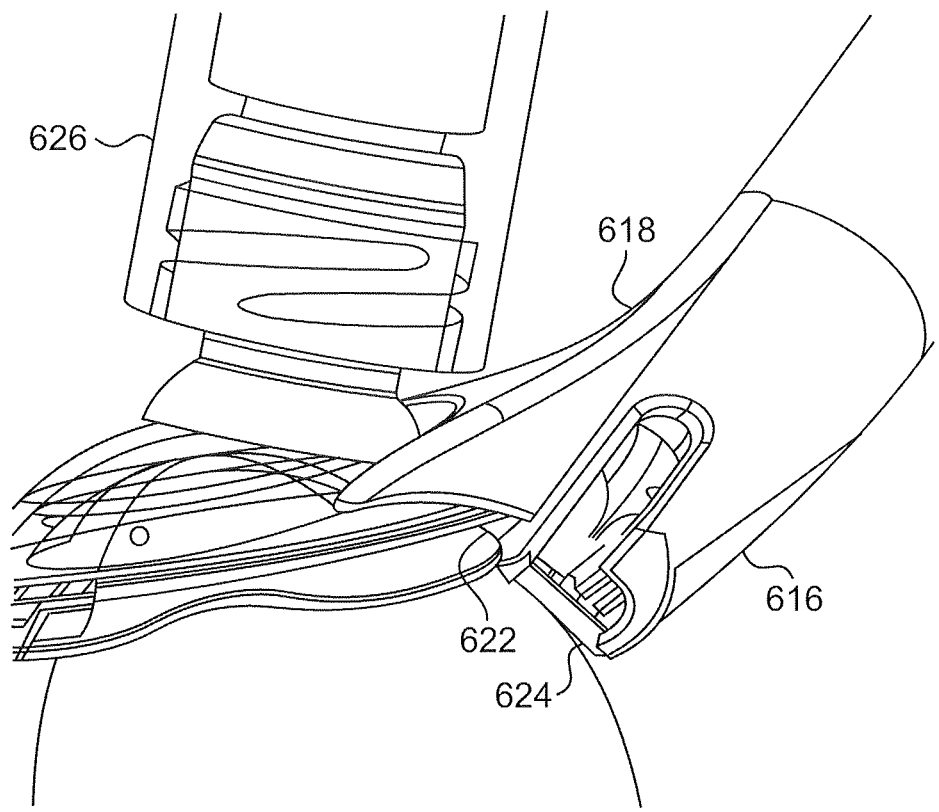

FIGS. 6A through 6C illustrate a fifth example ocular fixation device 600 and an example use of the ocular fixation device 600 in accordance with this disclosure. The embodiment of the ocular fixation device 600 and its use shown in FIGS. 6A through 6C are for illustration only. Other embodiments of the ocular fixation device 600 and uses of the ocular fixation device 600 could be used without departing from the scope of this disclosure.

As shown in FIG. 6A, the ocular fixation device 600 is similar to other ocular fixation devices described above. The ocular fixation device 600 includes a base 602, a dome 604, and locking rings 606-608. In this example, the base 602 is attached or secured to the dome 604 (or vice versa), and the locking rings 606-608 are secured between the base 602 and the dome 604. In this particular example, the locking ring 606 includes multiple sets of teeth (which could have different heights from the surface of a patient's eye), and these teeth correspond to multiple sets of teeth of the locking ring 608. As with the ocular fixation device 500, the locking rings 606-608 also include tabs 610-612, respectively, which extend outside of the base 602 and the dome 604 and can be used to control the opening and closing of the teeth on the locking rings 606-608.

As shown here, the dome 604 of the ocular fixation device 600 includes holes 614. The holes 614 in this example are used to align a surgical tool 616 to one or more locations of a patient's eye. The surgical tool 616 includes an alignment portion 618, which has two extensions 620a-620b forming a partial circle around the ocular fixation device 600. Each of the extensions 620a-620b includes an end that can be inserted into one of the holes 614 of the ocular fixation device 600. As shown in FIGS. 6B and 6C, the alignment portion 618 of the surgical tool 616 also includes a stopper 622, which can be depressed against the base 602 of the ocular fixation device 600. Collectively, the ends of the extensions 620a-620b and the stopper 622 represent three points that can be used to ensure the proper positioning of the surgical tool 616 on the patient's eye.

In this example, the surgical tool 616 includes two rotatable grasping clasps 624 with multiple tines. As shown in FIG. 6B, the grasping clasps 624 could be opened before the surgical tool 616 is pressed onto the patient's eye. As shown in FIG. 6C, when the surgical tool 616 is pressed onto the patient's eye, the grasping clasps 624 rotate (either inward or outward). This helps to secure the surgical tool 616 in place on the patient's eye. The two clasps could be independent appendages or part of one piece or appendage with multiple tines at each end.

In this example embodiment, the extensions 620a-620b of the surgical tool 616 form a partial circle around the ocular fixation device 600. This allows the surgical tool 616 to be attached or mounted to the ocular fixation device 600 while leaving a large portion of the dome 604 exposed. Among other things, this may allow the use of a positioning tool 626, which can be used to place the ocular fixation device 600 into one or more positions on the patient's eye. Additional details regarding an example positioning tool are provided below.

Although FIGS. 6A through 6C illustrate a fifth example of an ocular fixation device 600 and an example use of the ocular fixation device 600, various changes may be made to FIGS. 6A through 6C. For example, the relative sizes and dimensions of the features of the ocular fixation device 600 are for illustration only and can be altered in any suitable manner. Also, the guide mechanisms described above (the holes 614 in the dome 604 and the alignment portion 618 of the surgical tool 616) could be used with any other ocular fixation device and any other surgical tool.

Figure 7:
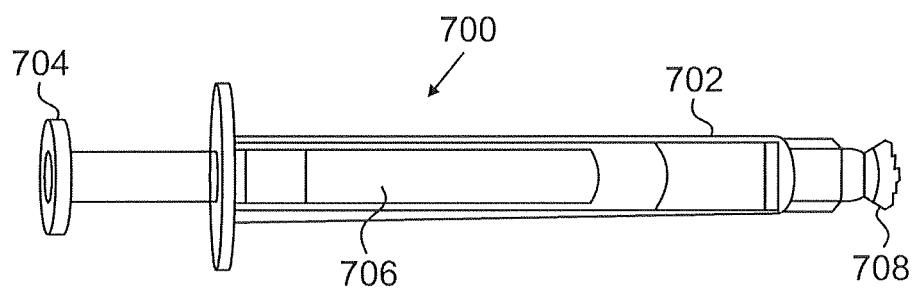
FIG. 7 illustrates an example positioning tool for use with an ocular fixation device in accordance with this disclosure.

FIG. 7 illustrates an example positioning tool 700 for use with an ocular fixation device in accordance with this disclosure. The embodiment of the positioning tool 700 shown in FIG. 7 is for illustration only. Other embodiments of the positioning tool 700 could be used without departing from the scope of this disclosure.

In this example embodiment, the positioning tool 700 represents a syringe structure having a body 702, a plunger 704 inserted into the body 702, a spring 706, and a suction cup 708. The spring 706 can bias the plunger 704 in the closed position, meaning the spring 706 moves the plunger 704 towards the suction cup 708 at the end of the body 702 (although the spring 706 could also bias the plunger 704 in the open position). The end of the plunger 704 can form an air-tight seal within the body 702, and the suction cup 708 can form an air-tight seal with an ocular fixation device.

To place an ocular fixation device on a patient's eye, the surgeon peers through the clear protective dome (or through the interior edge of the ring if no dome is attached) and centers the fixation device on the limbus or cornea, such as by using suitable landmarks from the eye (including any markings that may be placed on the eye in advance by the surgeon or other personnel). Once centered, the surgeon or other personnel may use a specialized tool to close the tabs and lock the rings in place or may manually lock the rings in place to firmly attach the fixation device to the eye. The surgeon or other personnel may use any other suitable technique to lock the fixation device in a centered position in the eye. Once attached to the eye, the surgeon or other personnel can then rotate a portion of the fixation device back under the patient's eyelid, exposing sufficient space on the forward part of the fixation device and the clear dome to attach the positioning tool to the clear dome. The positioning tool can be attached in the quadrant of the dome that is closest to the quadrant that the surgeon intends to create a tunnel in. Prior to attempting to attach the positioning device, the plunger 704 can be depressed (moved towards the suction cup), such as by the surgeon or other personnel, aided by the spring 706. The suction cup 708 can then be placed on the ocular fixation device, such as on the dome (if any) of the ocular fixation devices described above. The surgeon or other personnel then retracts the plunger 704 from the body 702 of the positioning device, allowing the plunger 704 to move away from the suction cup 708. The air-tight seals create a vacuum within the body 702 of the positioning tool 700, causing the suction cup 708 to attach to the ocular fixation device. A separate locking mechanism can lock the plunger 704 in place to maintain the vacuum during creation of the tunnel. Conversely, the spring 706 can be placed between the plunger 704 and the suction cup 708 in the body of the positioning device 702, thereby eliminating the need for a separate locking mechanism for the plunger 704 since the spring 706 may independently maintain pressure to hold the vacuum. Once the positioning device is firmly attached to the clear dome of the ocular fixation device, the positioning tool can be used to control and stabilize the eye (like a handle) while a surgical tool is simultaneously attached to the fixation device for the creation of the scleral tunnel. Once the tunnel has been successfully created using the surgical device, the plunger 704 of the positioning device can be depressed. This releases the suction cup 708 from the ocular fixation device, allowing the fixation device to be repositioned under the eyelid in a different location, exposing a new quadrant of the clear dome for reattachment of the positioning device and then reattachment of the surgical device for creation of the next tunnel.

This type of positioning tool 700 represents only one example of the types of tools that could be used to position and control an ocular fixation device. Any other suitable mechanism could be used to position and control an ocular fixation device. For example, an ocular fixation device could include a handle, such as a flip-ring that can be used to position and control the ocular fixation device and that can be rotated to the side and laid on the dome or base of the ocular fixation device. Any other suitable handle or other mechanism could be used to allow the ocular fixation device to be handled and positioned.

Although FIG. 7 illustrates one example of a positioning tool 700 for use with an ocular fixation device, various changes may be made to FIG. 7. For example, any other suitable device or technique could be used to position and control an ocular fixation device on a patient's eye.

FIG. 8 illustrates a sixth example ocular fixation device 800 in accordance with this disclosure. The embodiment of the ocular fixation device 800 shown in FIG. 8 is for illustration only. Other embodiments of the ocular fixation device 800 could be used without departing from the scope of this disclosure.

In this example, the ocular fixation device 800 includes a base 802, a fixation mechanism 804, and a handle 806. The base 802 may generally be pressed against a patient's eye, such as by pressing the base 802 down on the patient's cornea. The fixation mechanism 804 can then be attached to the patient's sclera, fixing the tool 800 in place and providing clear access to the patient's sclera. The fixation mechanism 804 could use any suitable technique to latch onto the patient's eye, such as prongs that can be forced into the patient's scleral tissue. The handle 806 can be used to raise and lower the fixation mechanism 804 after the base 802 has been pressed onto the patient's eye.

Although FIG. 8 illustrates a sixth example ocular fixation device 800, various changes may be made to FIG. 8. For example, any suitable mechanisms could be used to attach or otherwise associate the ocular fixation device 800 to the patient's eye.

FIGS. 9A through 9C illustrate a seventh example ocular fixation device 900 and an example use of the ocular fixation device 900 in accordance with this disclosure. The embodiment of the ocular fixation device 900 and its use shown in FIGS. 9A through 9C are for illustration only. Other embodiments of the ocular fixation device 900 and uses of the ocular fixation device 900 could be used without departing from the scope of this disclosure.

As shown in FIGS. 9A through 9C, the ocular fixation device 900 includes a central portion 902, a support 904 having a tool connection 906, and prongs 908. In some embodiments, the central portion 902 of the ocular fixation device 900 generally fits over the patient's cornea or some other portion of the patient's eye. The central portion 902 of the ocular fixation device 900 may also be centered on the patient's eye. The support 904 may be removably attached to the central portion 902, and the tool connection 906 allows a surgical tool 910 to be attached to the support 904. Alternatively, the support 904 could be attached with an axial pin to the center of the fixation device and rotate or swivel to the next quadrant.

The prongs 908 hold the central portion 902 of the ocular fixation device 900 in place on the patient's eye. For example, the prongs 908 could be extended out as shown in FIG. 9A prior to placement on the patient's eye. The prongs 908 could then be pushed or rotated so that the ends of the prongs 908 attach or secure to the patient's eye and could be held in the closed position by, for example, internal springs or wire mechanisms.

In particular embodiments, the support 904 can be attached in one orientation to the central portion 902, the surgical tool 910 can be attached to the support 904, and a scleral tunnel can be formed. This process could then be repeated, with the support 904 being removed and attached in a different orientation to the central portion 902 so that the surgical tool 910 can form a scleral tunnel at another location on the patient's eye. Alternatively, the support 904 could be attached with an axial pin to the center of the fixation device 902 and rotate or swivel to the next quadrant for creation of the next tunnel.

Although FIGS. 9A through 9C illustrate a seventh example ocular fixation device 900 and an example use of the ocular fixation device 900, various changes may be made to FIGS. 9A through 9C. For example, the ocular fixation device 900 could include other mechanisms for attachment to the patient's eye or to a surgical tool 910.

FIGS. 10A through 10D illustrate an eighth example ocular fixation device 1000 in accordance with this disclosure. The embodiment of the ocular fixation device 1000 shown in FIGS. 10A through 10D is for illustration only. Other embodiments of the ocular fixation device 1000 could be used without departing from the scope of this disclosure.

Figure 10A:
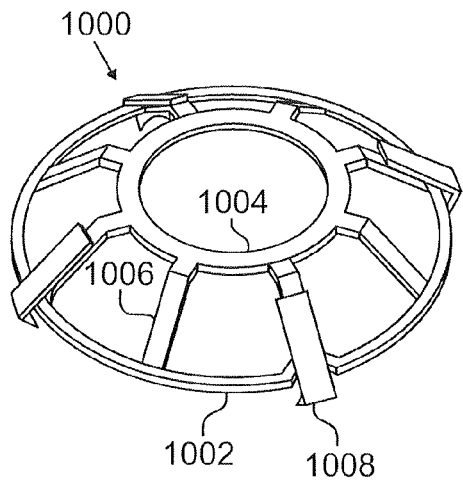
FIGS. 10A through 10D illustrate an eighth example ocular fixation device in accordance with this disclosure.

In this example, the ocular fixation device 1000 includes an outer ring 1002, an inner ring 1004, and ring connections 1006. The outer and inner rings 1002-1004 represent generally circular-shaped structures. As shown in FIG. 10A, the outer ring 1002 is generally in a different plane than the smaller inner ring 1004. The ring connections 1006 generally couple the outer and inner rings 1002-1004 together, forming an integrated structure. The ring connections 1006 are shaped such that a portion of a patient's eye can fit through the outer ring 1002 and approach or contact the inner ring 1004.

Figure 10B:
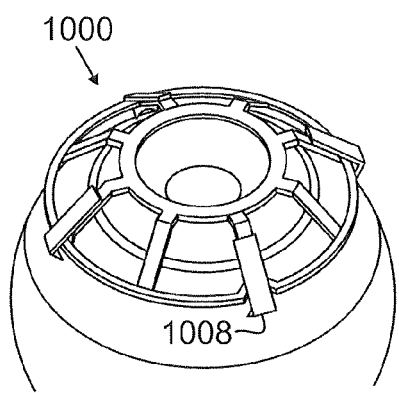
Figure 10C:
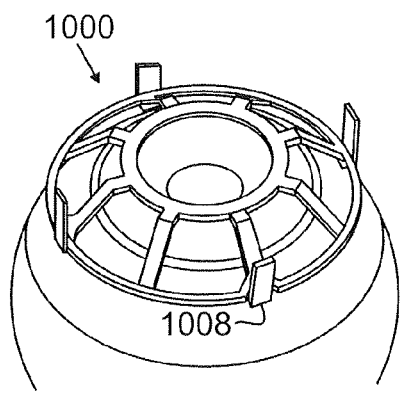
Figure 10D:
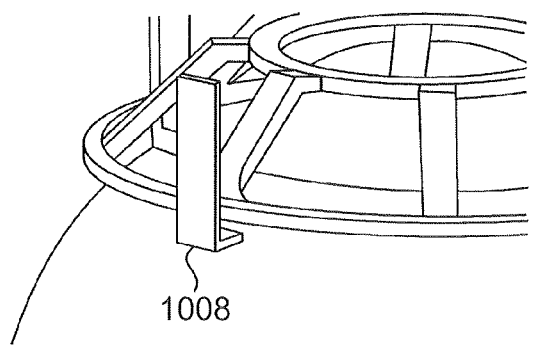

As shown here, the ocular fixation device 1000 also includes multiple prongs 1008, which are rotatably coupled to the outer ring 1002. As shown in FIG. 10B, the prongs 1008 can be opened prior to placement of the ocular fixation device 1000 on the patient's eye. As shown in FIGS. 10C and 10D, once placed on the patient's eye, each of the prongs 1008 can be rotated such that the ends of the prongs 1008 attach or secure to the patient's eye. To release the ocular fixation device 1000, the prongs 1008 can be rotated again to remove the ends of the prongs 1008 from the patient's eye. In some embodiments, the prongs could be held in place, such as by external springs or tensil wire built into the second or outer rings with constant tension to hold them in the closed and locked position while attached to the ocular tissue.

Although FIGS. 10A through 10D illustrate an eighth example ocular fixation device 1000, various changes may be made to FIGS. 10A through 10D. For example, the rings 1002-1004 could have any suitable dimensions, and the inner ring 1004 could have any suitable distance from the outer ring 1002. Also, any suitable mechanisms could be used to couple the rings 1002-1004 together and to attach or otherwise associate the ocular fixation device 1000 to the patient's eye.

Figure 11A:
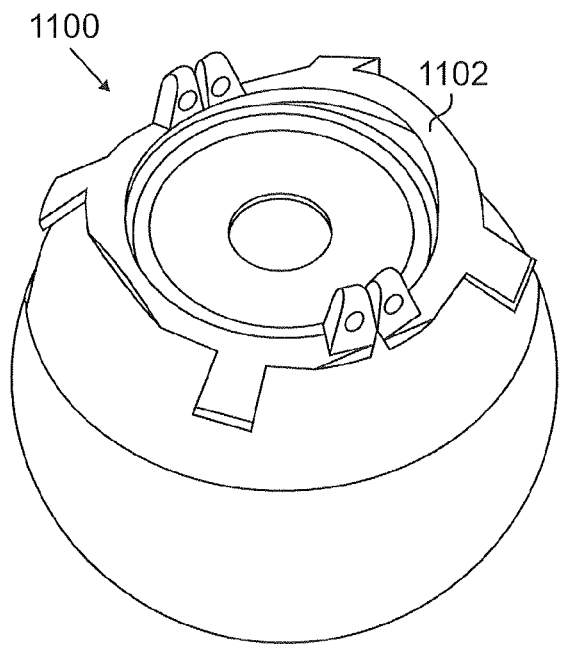
FIGS. 11A and 11B illustrate a ninth example ocular fixation device in accordance with this disclosure.
Figure 11B:
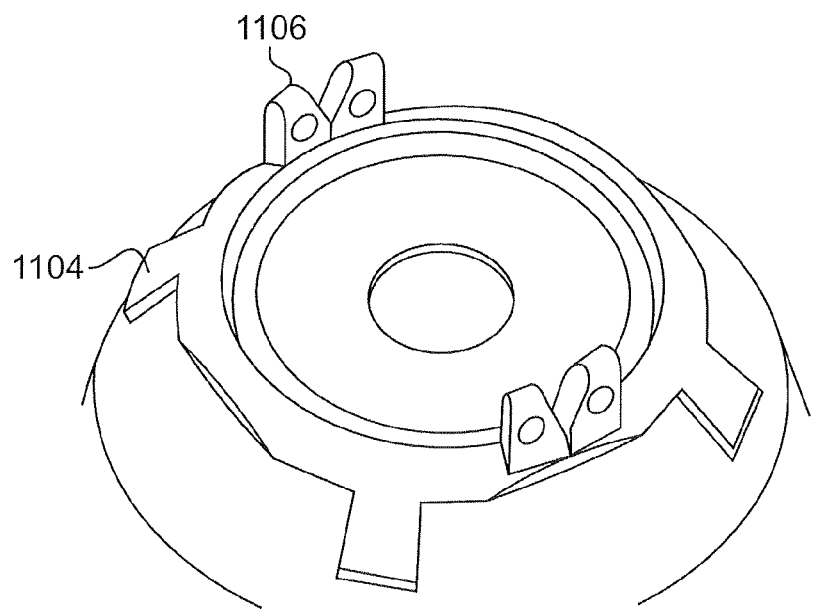

FIGS. 11A and 11B illustrate a ninth example ocular fixation device 1100 in accordance with this disclosure. The embodiment of the ocular fixation device 1100 shown in FIGS. 11A and 11B is for illustration only. Other embodiments of the ocular fixation device 1100 could be used without departing from the scope of this disclosure.

In this example, the ocular fixation device 1100 is formed from two rotatable segments 1102. Each segment 1102 includes prongs 1104 that can fix the segment 1102 to a patient's eye, such as in the sclera of the eye. Each segment 1102 also includes connection points 1104, which represent areas where other components (such as a surgical tool) can be attached to the ocular fixation device 1100. In addition, the ocular fixation device 1100 can provide reference markers identifying where scleral tunnels should be formed in the patient's eye, such as at locations at or between the prongs 1104. In some embodiments, one of the segments 1102 can be attached to the patient's eye, and then the other segment 1102 can be rotated out and attached to the patient's eye.

Although FIGS. 11A and 11B illustrate a ninth example ocular fixation device 1100, various changes may be made to FIGS. 11A and 11B. For example, each rotatable segment 1102 could include any suitable number of prongs 1104.

Figure 12A:
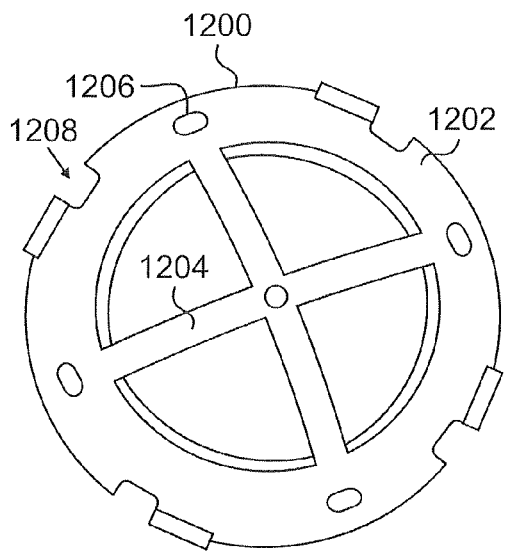
FIGS. 12A and 12B illustrate a tenth example ocular fixation device in accordance with this disclosure.
Figure 12B:
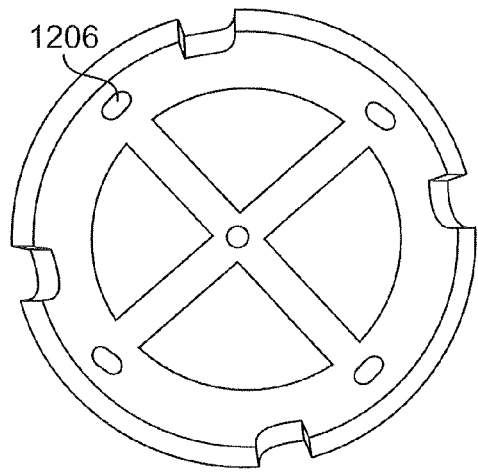
Figure 16A:
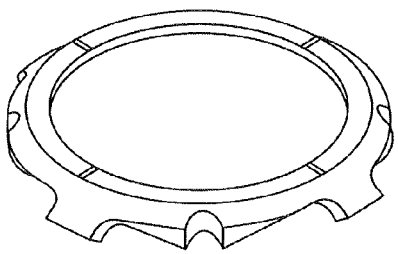
FIGS. 16A through 18B illustrate conventional ocular fixation tools.
Figure 16B:
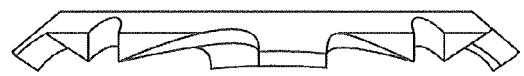

FIGS. 12A and 12B illustrate a tenth example ocular fixation device 1200 in accordance with this disclosure. The embodiment of the ocular fixation device 1200 shown in FIGS. 12A and 12B is for illustration only. Other embodiments of the ocular fixation device 1200 could be used without departing from the scope of this disclosure.

In this example, the ocular fixation device 1200 generally includes a ring 1202 with crossbars 1204. The ring 1202 is generally sized and shaped to lie on a patient's eye, such as by having a slanted inner edge that generally lies on the sclera of the patient's eye. The crossbars 1204 are generally sized and shaped to allow a portion of the patient's eye to fit through the ring 1202 and approach or contact the crossbars 1204.

In this example embodiment, twist picks 1206 are provided along the ring 1202. The twist picks 1206 represent screw-type structures that can attach to and release the ocular tissue of the patient's eye. For example, rotating the twist picks 1206 in one direction may attach the twist picks 1206 to the ocular tissue of the patient's eye. Rotating the twist picks 1206 in the opposite direction may release the ocular tissue. In this way, the ring 1202 can be attached to the patient's eye through simple rotation of the twist picks 1206.

As shown here, the ocular fixation device 1200 also includes connection points 1208. The connection points 1208 generally represent areas where, for example, a surgical tool for forming scleral incisions can be mounted on the ocular fixation device 1200. In this example, each of the connection points 1208 includes an elevated area of the ring 1202 adjacent to a notch in the ring 1202. However, any other suitable mechanism could be used to mount or otherwise couple any suitable surgical tool to the ocular fixation device 1200.

Although FIGS. 12A and 12B illustrate a tenth example ocular fixation device 1200, various changes may be made to FIGS. 12A and 12B. For example, the ring 1202 and the crossbars 1204 could have any suitable shape or dimensions, and the crossbars 1204 could join at any suitable height above the ring 1202. Also, any suitable mechanisms could be used to attach or otherwise associate the ocular fixation device 1200 to the patient's eye.

FIGS. 13A through 13D illustrate an eleventh example ocular fixation device 1300 in accordance with this disclosure. The embodiment of the ocular fixation device 1300 shown in FIGS. 13A through 13D is for illustration only. Other embodiments of the ocular fixation device 1300 could be used without departing from the scope of this disclosure.

Figure 13A:
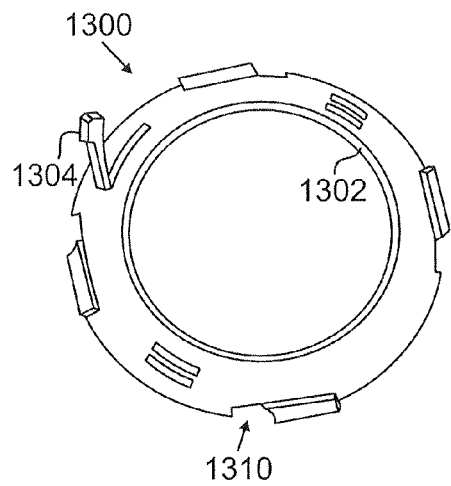
FIGS. 13A through 13D illustrate an eleventh example ocular fixation device in accordance with this disclosure.
Figure 13B:
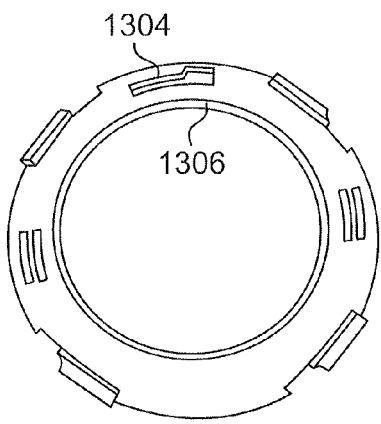
Figure 13C:
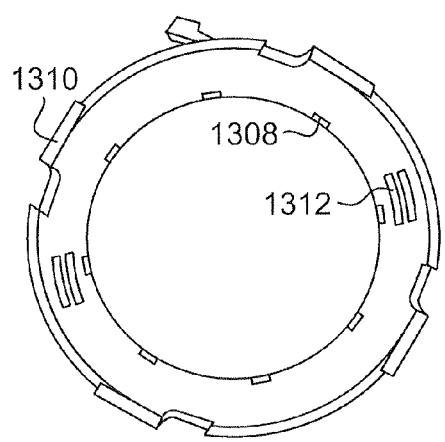
Figure 13D:
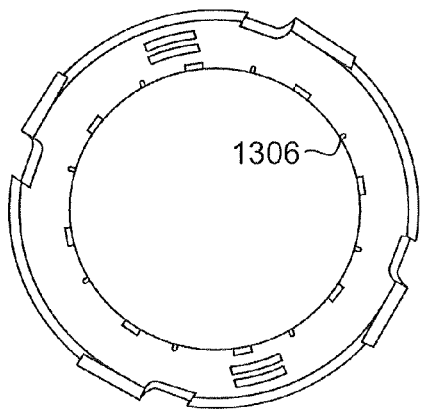

In this example, the ocular fixation device 1300 includes a ring 1302 having a lever 1304. The lever 1304 is used to control the movement of retractable pins 1306, which can be retracted into and extended out of the ring 1302. For example, the lever 1304 could be placed in the raised position as shown in FIG. 13A to retract the pins 1306 into the ring 1302. The ring 1302 could then be placed on the patient's eye and positioned properly. After that, the lever 1304 can be lowered as shown in FIG. 13B, causing the pins 1306 to extend from the ring 1302 and lock onto the patient's ocular tissue. For instance, the pins 1306 could penetrate the limbus of the patient's eye to a depth of 200 microns. Any suitable mechanism could be used to cause the pins 1306 to retract and extend under the control of the lever 1304.

In this example embodiment, the ocular fixation device 1300 could also include vertical teeth 1308, which may or may not penetrate the surface of the patient's eye. If the vertical teeth 1308 do not penetrate the surface of the patient's eye, the vertical teeth 1308 could still grip the patient's eye and provide lateral fixation, meaning the vertical teeth 1308 may help to prevent sideways motion of the ocular fixation device 1300 on the patient's eye. In addition, as with various prostheses described above, the ocular fixation device 1300 can include one or more connection points 1310 and one or more windows 1312.

Although FIGS. 13A through 13D illustrate an eleventh example ocular fixation device 1300, various changes may be made to FIGS. 13A through 13D. For example, the ring 1302, lever 1304, pins 1306, and other elements could have any suitable shape or dimensions. Also, any suitable mechanisms could be used to attach or otherwise associate the ocular fixation device 1300 to the patient's eye.

Figure 14A:
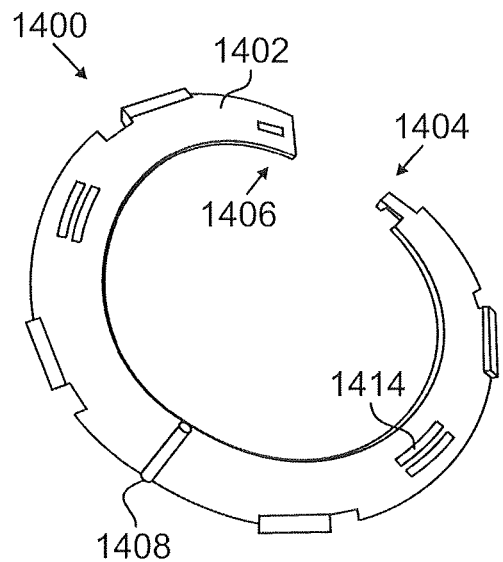
FIGS. 14A through 14C illustrate a twelfth example ocular fixation device in accordance with this disclosure.
Figure 14B:
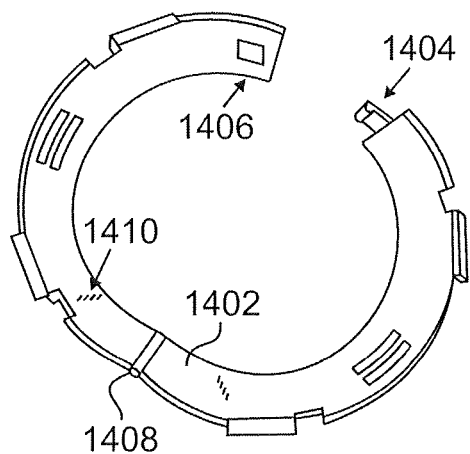
Figure 14C:
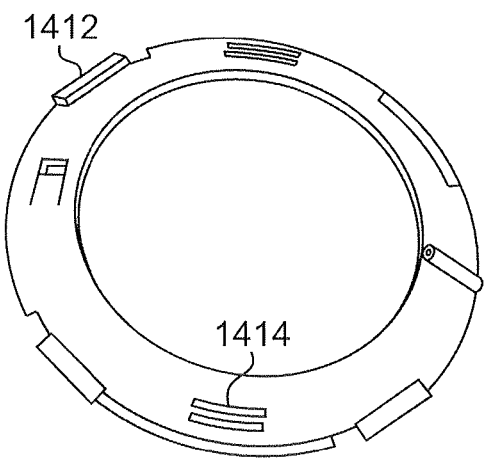

FIGS. 14A through 14C illustrate a twelfth example ocular fixation device 1400 in accordance with this disclosure. The embodiment of the ocular fixation device 1400 shown in FIGS. 14A through 14C is for illustration only. Other embodiments of the ocular fixation device 1400 could be used without departing from the scope of this disclosure.

In this example, the ocular fixation device 1400 includes a ring 1402 having a latch 1404 at one end and a receptacle 1406 at its other end. The ring 1402 also includes a hinge 1408, allowing two portions of the ring 1402 to open and close with respect to each other. In this embodiment, the portions of the ring 1402 can be pushed apart to open the ring 1402. The ring 1402 can be placed on a patient's eye, and the latch 1404 can be pushed into the receptacle 1406, forming a completed ring. As shown in FIG. 14B, the lower edge of the ring 1402 includes spikes 1410 that can dig into the ocular tissue of the patient's eye, securing the ring 1402 in place on the patient's eye.

As shown here, the ocular fixation device 1400 also includes connection points 1412, which generally represent areas where, for example, a surgical tool for forming scleral incisions can be mounted on the ocular fixation device 1400. Any suitable type of connection points or other mechanisms could be used to mount or otherwise couple any suitable surgical tool to the ocular fixation device 1400.

The ocular fixation device 1400 further includes one or more windows 1414. The windows 1414 allow a surgeon or other personnel to see through the ocular fixation device 1400 so as to determine the position of the ocular fixation device 1400 with respect to certain features of the patient's eye. For example, the windows 1414 could allow a surgeon to ensure that the ocular fixation device 1400 is attached to the area at or near the limbus of the patient's eye. The windows 1414 could have any suitable size, shape, and distribution in the ocular fixation device 1400.

Although FIGS. 14A through 14C illustrate a twelfth example ocular fixation device 1400, various changes may be made to FIGS. 14A through 14C. For example, the ring 1402, latch 1404, and receptacle 1406 could have any suitable shape or dimensions. Also, any suitable mechanisms could be used to attach or otherwise associate the ocular fixation device 1400 to the patient's eye.

For all of the ocular fixation devices described above, the various components or elements of the ocular fixation devices could have any suitable shapes, sizes, or dimensions. For example, various ones of the ocular fixation devices could have curved bottom surfaces, allowing the ocular fixation devices to generally lie on the surface of a patient's eye. Also, various elements or features of one of the ocular fixation devices could be used with others of the ocular fixation devices. Further, while often described as being attached to or otherwise associated with the patient's eye at the sclera or at the limbus, the ocular fixation devices could be attached to or otherwise associated with the patient's eye at other locations. In addition, the ocular fixation devices are often described as being used to support a surgical procedure involving the implantation of scleral prostheses into scleral tunnels in a patient's eye. However, any other suitable surgical procedure could be performed using the ocular fixation devices.

In particular embodiments, any of the ocular fixation devices described above could be sized such that the teeth, prongs, or other fixating means for associating the ocular fixation device with an eye are secured to, contact, are coupled to, or release tissue at or near the limbus of the eye. This region of the eye may be well-suited to this type of procedure as it heals rapidly. However, each of the ocular fixation devices could have any other suitable size or shape.

The use of various mechanisms have been described above for securing or fixating ocular tissue, such as rings or other devices having teeth, prongs, or pins. However, ocular fixation devices could use any suitable mechanism for securing or fixating ocular tissue. In this document, the phrases "means for fixating" and "fixating means" refer to any structure or portion thereof that extends from, projects from, forms a part of, or is otherwise associated with an ocular fixation device and that is pressed against, contacts, or penetrates the surface of a patient's eye. These "fixating means" include one or more teeth, prongs, pins, outcroppings, or other extensions or projections coupled to, attached to, extending from, integrated with, or otherwise associated with a ring or other structure placed proximate to the eye. The "fixating means" also include other mechanical structures such as one or more twist picks or sutures. In some embodiments, "fixating means" such as teeth may be planar or angled with respect to the structure with which the means are associated. Moreover, in this document, an ocular fixation device is said to be "associated with" an eye when the ocular fixation device is secured or attached to the eye.

Figure 15:
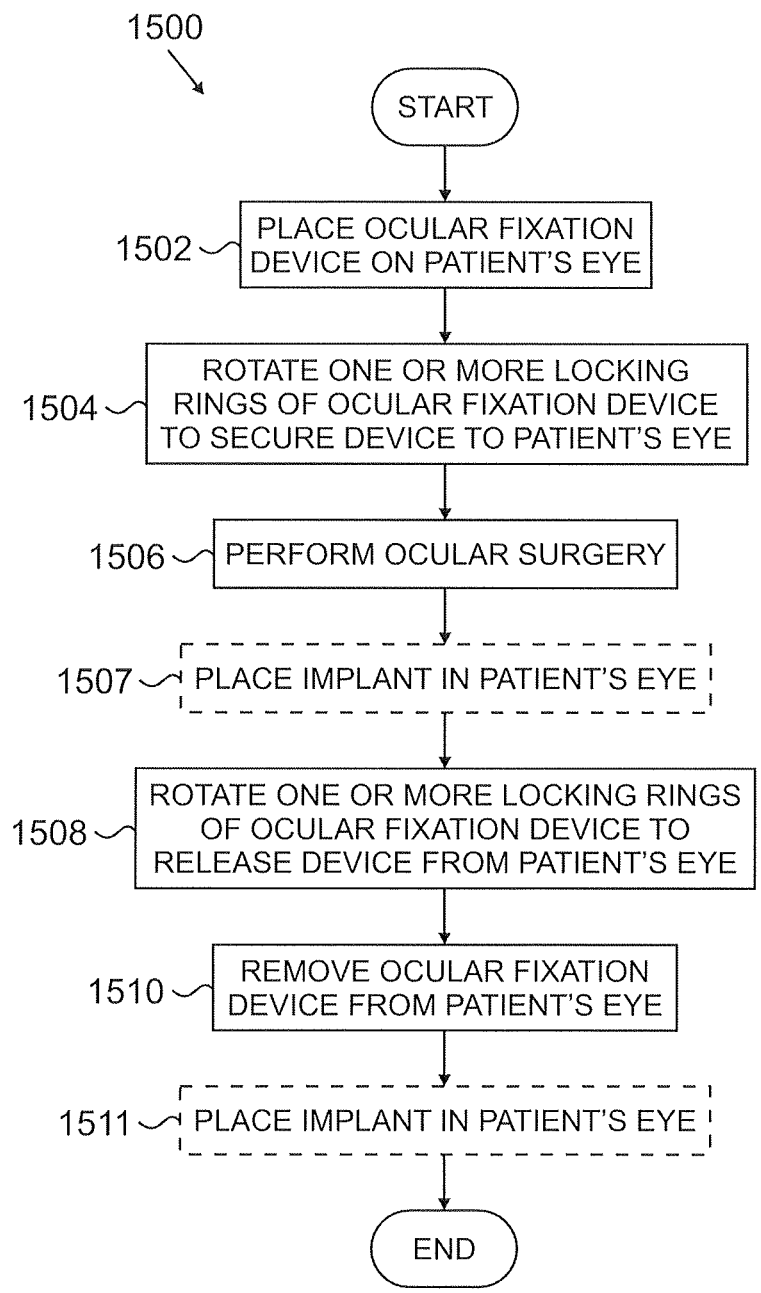
FIG. 15 illustrates an example method for ocular fixation in accordance with this disclosure.
Figure 17:
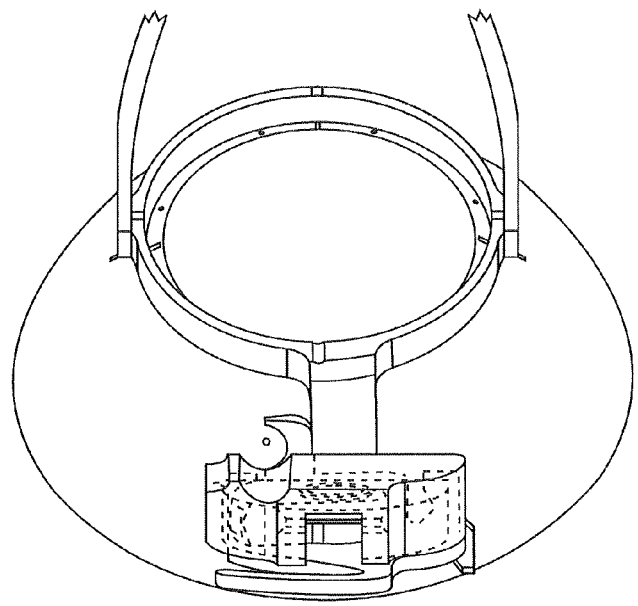
Figure 18A:
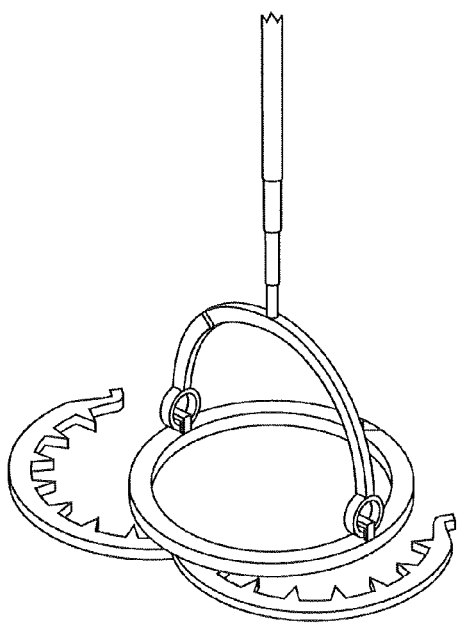
Figure 18B:
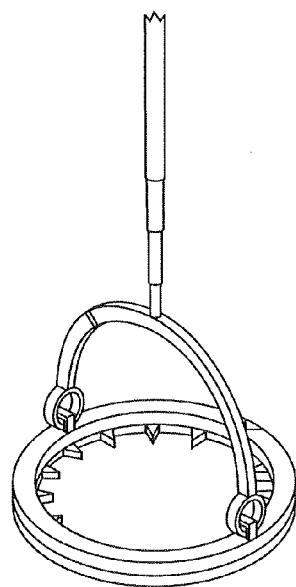

FIG. 15 illustrates an example method 1500 for ocular fixation in accordance with this disclosure. The embodiment of the method 1500 shown in FIG. 15 is for illustration only. Other embodiments of the method 1500 could be used without departing from the scope of this disclosure.

An ocular fixation device is placed on a patient's eye at step 1502. This could include, for example, placing any of the ocular fixation devices described above on the patient's eye. The ocular fixation device could include a dome so that the central portion of the patient's eye is covered and protected by the ocular fixation device.

One or more locking rings of the ocular fixation device are rotated to secure the ocular fixation device to the patient's eye at step 1504. This could include, for example, using an external tool to move one or more of the locking rings of the ocular fixation device. This could also include rotating one or more portions of the ocular fixation device to cause one or more of the locking rings to rotate. This could further include rotating one or more tabs coupled to one or more of the locking rings to cause one or more of the locking rings to rotate. Any other suitable technique could be used here to rotate one or more locking rings of the ocular fixation device.

An ocular surgical procedure occurs at step 1506. This could include, for example, forming one or more scleral tunnels in sclera of the patient's eye. Optionally, one or more scleral prostheses or other implants are placed in the patient's eye at step 1507. This could include, for example, inserting the scleral prostheses as the tunnels are being formed (as shown in FIGS. 4F through 4I above). This could also include inserting the scleral prostheses into the tunnels manually or otherwise after a surgical tool has been mounted on the ocular fixation device and used to form the scleral tunnels.

One or more locking rings of the ocular fixation device are rotated to release the ocular fixation device from the patient's eye at step 1508. This could include, for example, using an external tool, one or more portions of the ocular fixation device, or tabs coupled to the locking rings to rotate one or more of the locking rings. The ocular fixation device is removed from the patient's eye at step 1510. Optionally, one or more scleral prostheses or other implants are placed in the patient's eye at step 1511. This could include, for example, inserting the scleral prostheses into the tunnels manually or otherwise after the ocular fixation device has been removed from the patient's eye. One or both of the optional steps 1507 and 1511 show that the ocular fixation device can be used in a variety of ways during a surgical procedure.

Although FIG. 15 illustrates one example of a method 1500 for ocular fixation, various changes may be made to FIG. 15. For example, any suitable surgical procedure could involve the use of ocular fixation. Also, the surgical procedure may, but need not, involve the implantation of one or more scleral prostheses or other implants or elements into the patient's eye. Further, while described as rotating one or more locking rings to secure and release the patient's eye, other techniques (such as those associated with other embodiments of the ocular fixation devices described above) could be used.

It may be advantageous to set forth definitions of certain words and phrases used throughout this patent document. The terms "include" and "comprise," as well as derivatives thereof, mean inclusion without limitation. The term "or" is inclusive, meaning and/or. The term "ring" refers to a structure that is generally circular or ovoidal in shape.

While this disclosure has described certain embodiments and generally associated methods, alterations and permutations of these embodiments and methods will be apparent to those skilled in the art. For example, while shown as providing for the manual rotation or movement of one or more rings or other structures in an ocular fixation device, any suitable technology, such as a mechanical or electrical mechanism, could be used to rotate or move one or more rings or other structures in an ocular fixation device. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
  a first ring comprising first projections configured to contact ocular tissue of an eye; and
  a second ring comprising second projections configured to contact the ocular tissue of the eye;
  wherein the first and second projections are arranged to contact an outer surface of the eye;
  wherein the first and second projections are also arranged to grasp the ocular tissue of the eye between the first and second projections based on a first rotation of at least one of the rings that narrows a spacing between each first projection and an adjacent second projection;
  wherein the first and second projections are further arranged to release the ocular tissue of the eye based on a second rotation of at least one of the rings that widens the spacing between each first projection and its adjacent second projection; and
  wherein each first projection and its adjacent second projection are angled towards each other.

2. The apparatus of claim 1, wherein the first and second projections are arranged to grasp the ocular tissue of the eye in an area of the eye associated with a limbus of the eye.

3. The apparatus of claim 1, further comprising:
  a housing in which the first and second rings are housed; and
  a retaining ring within the housing and configured to retain the first and second rings in the housing.

4. The apparatus of claim 3, wherein the housing comprises a dome configured to protect a central portion of the eye.

5. The apparatus of claim 1, further comprising:
a base configured to be placed on the ocular tissue of the eye, the base further configured to retain the first and second rings; and
a dome configured to protect a central portion of the eye.

6. The apparatus of claim 5, wherein at least one of the first and second rings comprises one or more tabs that extend outside of the dome and the base, the one or more tabs configured to rotate at least one of the first and second rings.

7. The apparatus of claim 5, wherein the dome comprises one or more holes configured to receive one or more third projections from a surgical tool so as to align the surgical tool with at least one specified position on the eye.

8. The apparatus of claim 5, wherein the base includes one or more notches, each notch configured to receive a third projection from a surgical tool so as to align the surgical tool with at least one specified position on the eye.

9. The apparatus of claim 8, wherein the base includes one or more portions that are configured to lie on the eye, the one or more portions including one or more edges configured to allow a base of the surgical tool to be aligned against one of the edges when the third projection from the surgical tool is inserted into one of the notches.

10. The apparatus of claim 1, wherein one of:
the first and second rings are substantially planar;
the first and second rings are curved along inner edges of the rings; and
the first and second rings extend substantially along an axis through a center of the rings.

11. The apparatus of claim 1, wherein the first and second projections comprise at least one of: teeth, prongs, spikes, and pins.

12. The apparatus of claim 1, wherein the first and second projections are configured, when grasping the ocular tissue of the eye, to secure the apparatus to the outer surface of the eye and to restrain movement of the eye.

13. The apparatus of claim 1, wherein at least one of the rings is configured to rotate about an axis through a center of the rings.

14. A system comprising:
an ocular fixation device comprising:
a first ring comprising first projections configured to contact ocular tissue of an eye; and
a second ring comprising second projections configured to contact the ocular tissue of the eye;
wherein the first and second projections are arranged to contact an outer surface of the eye;
wherein the first and second projections are also arranged to grasp the ocular tissue of the eye between the first and second projections based on a first rotation of at least one of the rings that narrows a spacing between each first projection and an adjacent second projection;
wherein the first and second projections are further arranged to release the ocular tissue of the eye based on a second rotation of at least one of the rings that widens the spacing between each first projection and its adjacent second projection; and
wherein each first projection and its adjacent second projection are angled towards each other; and
a surgical tool mountable on the ocular fixation device.

15. The system of claim 14, wherein the surgical tool comprises a surgical blade configured to form a scleral tunnel in the ocular tissue of the eye.

16. The system of claim 14, wherein the first and second projections are arranged to grasp the ocular tissue of the eye in an area of the eye associated with a limbus of the eye.

17. The system of claim 14, wherein the ocular fixation device further comprises:
a housing in which the first and second rings are housed; and
a retaining ring within the housing configured to retain the first and second rings in the housing.

18. The system of claim 14, wherein the ocular fixation device further comprises:
a base configured to be placed on the ocular tissue of the eye, the base further configured to retain the first and second rings; and
a dome configured to protect a central portion of the eye.

19. The system of claim 18, wherein at least one of the first and second rings comprises one or more tabs that extend outside of the dome and the base, the one or more tabs configured to rotate at least one of the first and second rings.

20. The system of claim 18, wherein the dome comprises one or more holes configured to receive one or more third projections from the surgical tool so as to align the surgical tool with at least one specified position on the eye.

21. The system of claim 18, wherein the base includes one or more notches, each notch configured to receive a third projection from the surgical tool so as to align the surgical tool with at least one specified position on the eye.

22. The system of claim 21, wherein the base includes one or more portions that are configured to lie on the eye, the one or more portions including one or more edges configured to allow a base of the surgical tool to be aligned against one of the edges when the third projection from the surgical tool is inserted into one of the notches.

23. The system of claim 14, wherein the ocular fixation device comprises a housing in which the first and second rings are housed, the surgical tool mountable on the housing.

24. The system of claim 14, wherein the first and second projections comprise at least one of: teeth, prongs, spikes, and pins.

25. An apparatus comprising:
a first ring comprising a plurality of first teeth configured to contact an outer surface of an eye; and
a second ring comprising a plurality of second teeth configured to contact the outer surface of the eye;
wherein the first and second teeth are arranged to grasp ocular tissue of the eye between the first and second teeth based on a first rotation of at least one of the rings that narrows a spacing between each first tooth and an adjacent second tooth;
wherein the first and second teeth are also arranged to release the ocular tissue of the eye based on a second rotation of at least one of the rings that widens the spacing between each first tooth and its adjacent second tooth; and
wherein each first tooth and its adjacent second tooth are angled towards each other.

26. An apparatus comprising:
a first ring comprising a plurality of first projections configured to contact an outer surface of an eye; and
a second ring adjacent to the first ring, the second ring comprising a plurality of second projections configured to contact the outer surface of the eye;
wherein the first and second rings are configured such that (i) a first rotation of at least one of the rings causes the first projections to move towards adjacent second projections to thereby narrow spacings between the first projections and the adjacent second projections and grasp ocular tissue of the eye between the first and second projections and (ii) a second rotation of at least one of the rings causes the first projections to move away from the adjacent second projections to thereby widen the spacings between the first projections and the adjacent second projections and release the ocular tissue of the eye; and wherein each first projection and its adjacent second projection are angled towards each other.

* * * * *

UNITED STATES PATENT AND TRADEMARK OFFICE
CERTIFICATE OF CORRECTION

| | | |
|---|---|---|
| PATENT NO. | : 8,709,029 B2 | Page 1 of 1 |
| APPLICATION NO. | : 11/827444 | |
| DATED | : April 29, 2014 | |
| INVENTOR(S) | : Griffish et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 234 days.

Signed and Sealed this
Twenty-eighth Day of July, 2015

Michelle K. Lee
*Director of the United States Patent and Trademark Office*